(12) United States Patent
Shibata et al.

(10) Patent No.: US 11,692,989 B2
(45) Date of Patent: Jul. 4, 2023

(54) USE OF SOIL AND OTHER ENVIRONMENTAL DATA TO RECOMMEND CUSTOMIZED AGRONOMIC PROGRAMS

(71) Applicant: Locus Solutions IPCo, LLC, Solon, OH (US)

(72) Inventors: Scott Alan Shibata, Irvine, CA (US); Paul S. Zorner, Encinitas, CA (US); Sean Farmer, North Miami Beach, FL (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 220 days.

(21) Appl. No.: 16/925,592

(22) Filed: Jul. 10, 2020

(65) Prior Publication Data

US 2021/0010993 A1 Jan. 14, 2021

Related U.S. Application Data

(60) Provisional application No. 62/872,806, filed on Jul. 11, 2019.

(51) Int. Cl.
*G01N 33/24* (2006.01)
*G06N 20/00* (2019.01)
(Continued)

(52) U.S. Cl.
CPC .......... *G01N 33/24* (2013.01); *A01B 79/005* (2013.01); *G06N 5/04* (2013.01); *G06N 20/00* (2019.01); *G01N 2033/245* (2013.01)

(58) Field of Classification Search
CPC .. G01N 33/24; G01N 2033/245; G06N 20/00; G06N 5/04; A01B 79/005
See application file for complete search history.

(56) References Cited

U.S. PATENT DOCUMENTS 9,175,258 B2 11/2015 Bywater-Ekegard et al.
10,109,024 B2 10/2018 Bakke et al.
(Continued)

FOREIGN PATENT DOCUMENTS

JP 2018113007 A 7/2018
KR 20180116639 A 10/2018
(Continued)

OTHER PUBLICATIONS

Domeignoz-Horta, L.A., et al., "Non-denitrifying nitrous oxide-reducing bacteria—An effective N2O sink in soil" Soil Biology & Biochemistry, 2016, 103: 376-379.
(Continued)

*Primary Examiner* — Alexander Satanovsky
*Assistant Examiner* — Lynda Dinh
(74) *Attorney, Agent, or Firm* — Saliwanchik, Lloyd & Eisenschenk

(57) ABSTRACT

Systems and methods are provided for classifying a microbiome at a geographic site where agricultural activity is, or will be, conducted in order to improve and/or promote agricultural productivity at the site. Machine learning and/or artificial intelligence classifier tools use DNA sequencing input data and environmental information to generate recommendations for customized soil and/or crop treatment compositions, irrigation practices, and/or other agricultural activity, to enhance plant health and crop productivity.

8 Claims, 4 Drawing Sheets

(51) Int. Cl.
    *G06N 5/04*     (2023.01)
    *A01B 79/00*     (2006.01)

(56) References Cited

U.S. PATENT DOCUMENTS

| | | |
|---|---|---|
| 10,251,347 B2 | 4/2019 | Xu et al. |
| 2005/0208593 A1 | 9/2005 | Vail et al. |
| 2006/0008921 A1 | 1/2006 | Daniels et al. |
| 2009/0029879 A1 | 1/2009 | Soni et al. |
| 2010/0044031 A1 | 2/2010 | Fallon et al. |
| 2011/0160090 A1 | 6/2011 | Cary |
| 2013/0324406 A1 | 12/2013 | Chisholm et al. |
| 2014/0170674 A1 | 6/2014 | He |
| 2014/0201870 A1 | 7/2014 | Harman |
| 2015/0219643 A1 | 8/2015 | Song et al. |
| 2016/0222442 A1 | 8/2016 | Cary |
| 2016/0356780 A1 | 12/2016 | Bell et al. |
| 2017/0107557 A1 | 4/2017 | Embree et al. |
| 2017/0159108 A1* | 6/2017 | Budding ............... C12Q 1/689 |
| 2018/0354830 A1 | 12/2018 | Ghylin |
| 2018/0363031 A1* | 12/2018 | Becares ............... C12Q 1/689 |
| 2019/0050741 A1 | 2/2019 | Mewes et al. |
| 2019/0112528 A1* | 4/2019 | Huang ................. A01N 65/03 |
| 2020/0354711 A1* | 11/2020 | Murray ................. C12N 1/06 |
| 2020/0381081 A1* | 12/2020 | Zajdband ............... C12N 1/06 |
| 2021/0315212 A1* | 10/2021 | Rezaei .................. C12N 1/04 |

FOREIGN PATENT DOCUMENTS

| | | |
|---|---|---|
| WO | 0068692 A1 | 11/2000 |
| WO | 2018049182 A2 | 3/2018 |
| WO | 2018094075 A1 | 5/2018 |
| WO | 2018132774 A1 | 7/2018 |
| WO | 2018213604 A2 | 11/2018 |
| WO | 2019023034 A2 | 1/2019 |
| WO | 2019023034 A3 | 1/2019 |
| WO | 2019067379 A1 | 4/2019 |
| WO | 2019067380 A2 | 4/2019 |
| WO | 2019067380 A3 | 4/2019 |
| WO | 2019089730 A1 | 5/2019 |
| WO | 2019140439 A1 | 7/2019 |
| WO | 2019168852 A1 | 9/2019 |
| WO | 2019217548 A2 | 11/2019 |
| WO | 2020076797 A1 | 4/2020 |
| WO | 2020076800 A1 | 4/2020 |
| WO | 2020112844 A1 | 6/2020 |
| WO | 2020210074 A1 | 10/2020 |
| WO | 2020219386 A1 | 10/2020 |
| WO | 2020219432 A1 | 10/2020 |

OTHER PUBLICATIONS

Thompson, L.R., et al., "A communal catalogue reveals Earth's multiscale microbial diversity." Nature, Nov. 2017, 551(7681): 457-463.

* cited by examiner

FIG. 4

USE OF SOIL AND OTHER ENVIRONMENTAL DATA TO RECOMMEND CUSTOMIZED AGRONOMIC PROGRAMS

CROSS-REFERENCE TO RELATED APPLICATION

This application claims priority to U.S. Provisional Patent Application No. 62/872,806, filed Jul. 11, 2019, which is incorporated herein by reference in its entirety.

BACKGROUND OF THE INVENTION

Many agricultural practices involve application of products comprising chemical and/or biological-based ingredients to crops and/or soil in order to enhance plant growth, health, and overall productivity. For example, pesticides and biopesticides can help protect plants from invaders such as arthropods, pathogenic microbes and competitive weeds; growth stimulants can stimulate the natural processes of a plant and/or its surrounding environment to enhance, for example, nutrient efficiency, tolerance to stressors, and quality of crop end products; and fertilizers and biofertilizers can provide and/or help provide nutrients to plants, most often through their roots.

Existing approaches to identifying an appropriate agricultural product and its optimal application for use with crops, fields and soils typically involve replicating experiments with products at multiple locations to assess the varying effectiveness given any number of environmental factors, such as crop type or climate. Additionally, in some instances, biological-based products comprise microorganisms, such as fungi and/or bacteria. The unique needs of living microorganisms can further complicate the discovery of the optimal application parameters for these types of products.

Identifying the required environmental factors impacting performance and producing locally-adapted recommendations is particularly challenging for soil-active agricultural products. Soil type, temperature, water retention and many other above- and below-ground environmental factors influence the performance of agricultural products, both through influence on a crop growing in the soil and influence on the endemic soil microbiome of a particular rhizosphere. Additionally, consideration should be taken when dealing with land that has a long history of use of certain chemical fertilizers, pesticides, herbicides, fungicides, and antibiotics, which can alter soil ecosystems.

The rhizosphere is the zone of soil wherein a plant's root system grows and absorbs water and nutrients. Existing within the rhizosphere are diverse microbial communities comprised of microbial species that coexist with each other and with plant roots to form a complex network of relationships. This community, or microbiome, performs a number of ecosystem functions that are necessary for plant growth and health, including fixing and cycling of nutrients, immune modulation, pest and disease control, water retention, and many others.

Microbial communities can also exist in and on aboveground plant parts, in water sources, and in the air. Endemic microbial community composition at a site has been shown to change across gradients of, for example, environment, geographic distance, salinity, temperature, oxygen, nutrients, pH, day length, and biotic factors. These patterns have been identified mostly by focusing on one sample type and region at a time, with insights extrapolated across environments and geography to produce generalized principles.

To assess how microbes are distributed across environments globally—or whether microbial community dynamics follow fundamental ecological laws at a planetary scale—requires either a large-scale monolithic cross-environment survey or a practical methodology for coordinating many independent metagenomic surveys. Metagenomics is the study of genetic material that has been recovered directly from environmental samples.

Conventional sequencing requires a culture of identical cells as a source of DNA. However, many microorganisms in environmental samples cannot be cultured and thus cannot be sequenced. Advances in bioinformatics, refinements of DNA amplification, and increases in computational power have greatly aided the analysis of DNA sequences recovered from environmental samples, allowing the adaptation of shotgun sequencing to the samples. The random nature of shotgun sequencing ensures that many of these organisms, which would otherwise go unnoticed using traditional culturing techniques, will be represented by at least some sequence segments, for example, function-indicating sequence segments.

Other microbiome DNA sequencing data can also be used for identifying microorganisms in a sample. For example, 16s and Internal Transcribed Spacer (ITS) ribosomal RNA (rRNA) sequencing are common amplicon sequencing methods used to identify and compare bacterial and fungal taxonomies, respectively, within a sample.

New studies of microbial environments are rapidly accumulating, and analyses of the data suggest robust general trends in microbial community composition, including the importance of environmental factors such as, for example, soil composition. These findings support the utility of DNA sequencing analysis to reveal basic patterns of microbial diversity and suggest that a scalable and accessible analytical framework is needed. (Thompson et al. 2017).

Notably, microbiome analyses could have the potential to vastly improve the way agricultural practices are conducted; however, objective data classifying the microbiome for a particular soil, plant, crop and/or region is generally unavailable and/or too cost-prohibitive to meaningfully produce at scale. Thus, data modelling methods and systems are needed, so that farmers and growers may analyze the microbiome(s) at a geographic site for a particular sample type (e.g., soil, plant, water and/or air), as well as other environmental factors, to develop products and agronomic practices for enhancing agricultural production and optimizing those practices for specific products.

BRIEF SUMMARY OF THE INVENTION

The subject invention provides systems and methods for classifying the microbiome(s) at a geographic site where agricultural activity is, or will be, conducted in order to, for example, improve and/or promote agricultural productivity at the site. In some embodiments, computer-implemented approaches are provided for developing one or more predictive models that analyze environmental information and DNA sequencing data from soil, plant, water and/or air samples at geographic sites in order to characterize the relationships between environment and the characteristics of the microbiome(s) present in the site's soil, plants, water and/or air.

More specifically, the subject invention utilizes a large sample set of diverse DNA sequencing input data, as well as environmental and microbial test information, to determine relationships between environmental factors and the identities, quantities and distributions of microbial species, taxonomies, gene functions and/or groupings thereof, at a chosen site. Machine learning and/or artificial intelligence classifier tools use this information to generate various output data, such as, for example, recommendations for customized formulations of soil and/or crop treatment compositions, application rate and/or timing for customized product compositions, fungicide/pesticide application rate and/or timing, irrigation practices, and/or other agricultural activity, to enhance plant health and crop productivity at the site.

Advantageously, in some embodiments, the subject methods allow for assessing the characteristics of a geographic site without the need for physical sampling at the site, and also without the need for expensive classification utilizing DNA sequencing methods. Thus, the process results in a broad, yet meaningful, dataset using a significantly lower cost methodology. In certain embodiments, however, sampling and/or microbial testing methodologies may be utilized.

In general, a computer system comprising a plurality of elements and modules, receives input data from a plurality of geographic sites to build a classification model and a predictive classification model, and generates output data (or "recommendations") from site-specific input data, wherein the output data is used by a farmer or grower (i.e., the "user") to alter the soil, plant, water and/or air microbiome in a variety of ways to achieve one or more agronomic goals. These goals can include, but are not limited to, improving yields, improving plant tolerance to abiotic and biotic stressors, minimizing the impact of plant diseases on crops, and others that are directed towards promoting agricultural productivity.

In one embodiment, the computer system receives a Training Data Set comprising broad soil, plant, water and/or air microbiome data, said microbiome data comprising DNA sequencing data derived from soil, plant, water and/or air samples taken from a plurality of geographic sites.

The DNA sequencing data can comprise "taxonomic DNA sequencing data," or sequencing data obtained from 16s and/or Internal Transcribed Spacer (ITS) sequencing of bacterial and fungal species, respectively. These data provide specific taxonomic-identifying information.

The DNA sequencing data can also comprise "functional DNA sequencing data," or metagenomic data obtained from, for example, shotgun sequencing. These data provide gene function-identifying information.

The computer system produces a microbiome classification model based on the relative frequencies of taxonomic-indicating and/or function-indicating gene markers from each sample.

In certain embodiments, the microbiome classification model is an unsupervised machine learning classifier ("UMLC"). The UMLC analyzes the Training Input Data, and then groups, or classifies, samples into "microbiome types." In certain embodiment, the classifications are based on similarities between the samples with regard to, for example, relative microbe species frequencies and/or relative gene function frequencies.

The computer system then receives one or more other sets of agronomic training input data from the plurality of geographic sites from where the Training Data Set was collected. In certain embodiments, the other agronomic training input data comprise "environmental" training data, such as, for example, soil type, soil characteristics, and/or crop type.

In one embodiment, the other agronomic training input data comprise "microbial test" training data, such as, for example, quantitative results from lab and/or in-field analysis of gene markers, microbe species, microbe-based agents and/or other analytes arising from the presence or activity of microbes, in samples.

The computer system then develops a supervised machine learning classifier ("SMLC") based on relationships drawn between the Training Data Set and the other agronomic training data from the plurality of geographic sites. More specifically, the SMLC draws from the microbiome "types" assigned by the UMLC and from the one or more other sets of agronomic training input data, to analyze site-specific prediction input data from a geographic site of interest. The SMLC then predicts the microbiome classification (or type(s)) at the specific geographic site.

In certain embodiments, the site-specific prediction input data comprises agronomic data collected from the geographic site, such as, for example, site-specific environmental data and/or site-specific microbial test data.

In some embodiments, the computer system further comprises a Recommendation Engine, which correlates microbiome classification and site-specific environmental data with an optimal agronomic program for a specific geographic site, and generates recommendations for agronomic programs at the site.

In one embodiment, an agronomic program can include, for example, a schedule or list of one or more agricultural activities to be conducted at a site to improve and/or promote agricultural productivity. Such activity can include, for example, type of plant(s) or crop(s) to grow; type and/or amount of fertilizer to apply, and timing/mode of application; type and/or amount of pesticides, fungicides and/or herbicides to apply, and timing/mode of application; amount of water to apply and timing/mode of irrigation; and/or soil conditioning, such as tilling, applying organic material, fumigating, and/or planting cover crops.

In one embodiment, an agronomic program provides for a customized formulation for a soil and/or crop treatment composition that, when applied to a plant, crop and/or the surrounding environment (e.g., the soil), provides a number of benefits to the plant and/or crop.

After receiving the recommendation for the customized formulation, a user can then obtain and apply the composition. Methods for producing and applying a soil treatment composition according to one embodiment of the subject invention are provided herein, although in certain embodiments, the Recommendation Engine can also generate a recommendation providing instructions for obtaining and/or applying a customized composition along with the recommendation providing the customized formulation. For example, a recommendation can further comprise optimal timing and/or rates of application for the product to ensure a positive impact on one or more agronomic metrics that can be influenced by the soil, plant, water and/or air microbiome type(s), including, for example, enhancement of plant health and growth, crop yield, disease protection, and/or flower and fruit timing.

In one exemplary embodiment, a customized soil treatment composition is provided, comprising one or more beneficial microorganisms and/or microbial growth by-products. The microorganisms can be selected from, for example, bacteria, yeasts and fungi that are capable of growing in soil, and that directly or indirectly confer one or more benefits to a plant growing in the soil. Such benefits can include, for example, enhanced health, growth and/or yields.

The soil treatment composition can further comprise, for example, residual nutrients and/or growth medium used for cultivation of the one or more microorganisms; an agriculturally-acceptable carrier, such as water; added nutrients and/or prebiotics to support the growth of the one or more beneficial microorganisms; and/or any other compatible additives for enhancing plant health, such as fertilizers, herbicides, pesticides and/or soil amendments.

In certain embodiments, the computer system can also recommend customized formulations for non-biological soil and/or crop treatment products. For example, the non-biological product(s) can comprise one or more chemical, inorganic and/or synthetic products for enhancing agricultural productivity.

Following the implementation of one or more recommended agronomic programs at a specific geographic site, the agronomic program(s) and associated results of implementation (e.g., changes in plant health, growth and/or yield) can be recorded and submitted back into the Recommendation Engine to further improve the recommendation capabilities of the system.

Advantageously, the subject methods are cost-effective and efficient methods for better understanding the microbiomes that impact agricultural productivity, and thereby achieve improved microbiomes in, for example, soil, plants, water, and/or the air, at a geographic site. Accordingly, the subject methods can help a grower achieve benefits resulting from improved microbiomes, including, for example, enhanced plant health; increased crop yields; enhanced quality of agricultural products; improved soil quality; enhanced soil carbon sequestration; reduced greenhouse gas emissions; reduced pest numbers; and treatment and/or prevention of plant diseases.

BRIEF DESCRIPTION OF THE FIGURES

FIG. 4 shows a visual representation of microbiome "types." Each hash mark along the x-axis represents a particular species, taxonomic unit or gene function. The relative darkness of shading for each hash mark represents the relative frequency of that species, taxonomic unit or gene function. Darker shades denote a greater relative frequency and lighter shades denote a lower relative frequency.

DETAILED DESCRIPTION OF THE INVENTION

Figure 1:
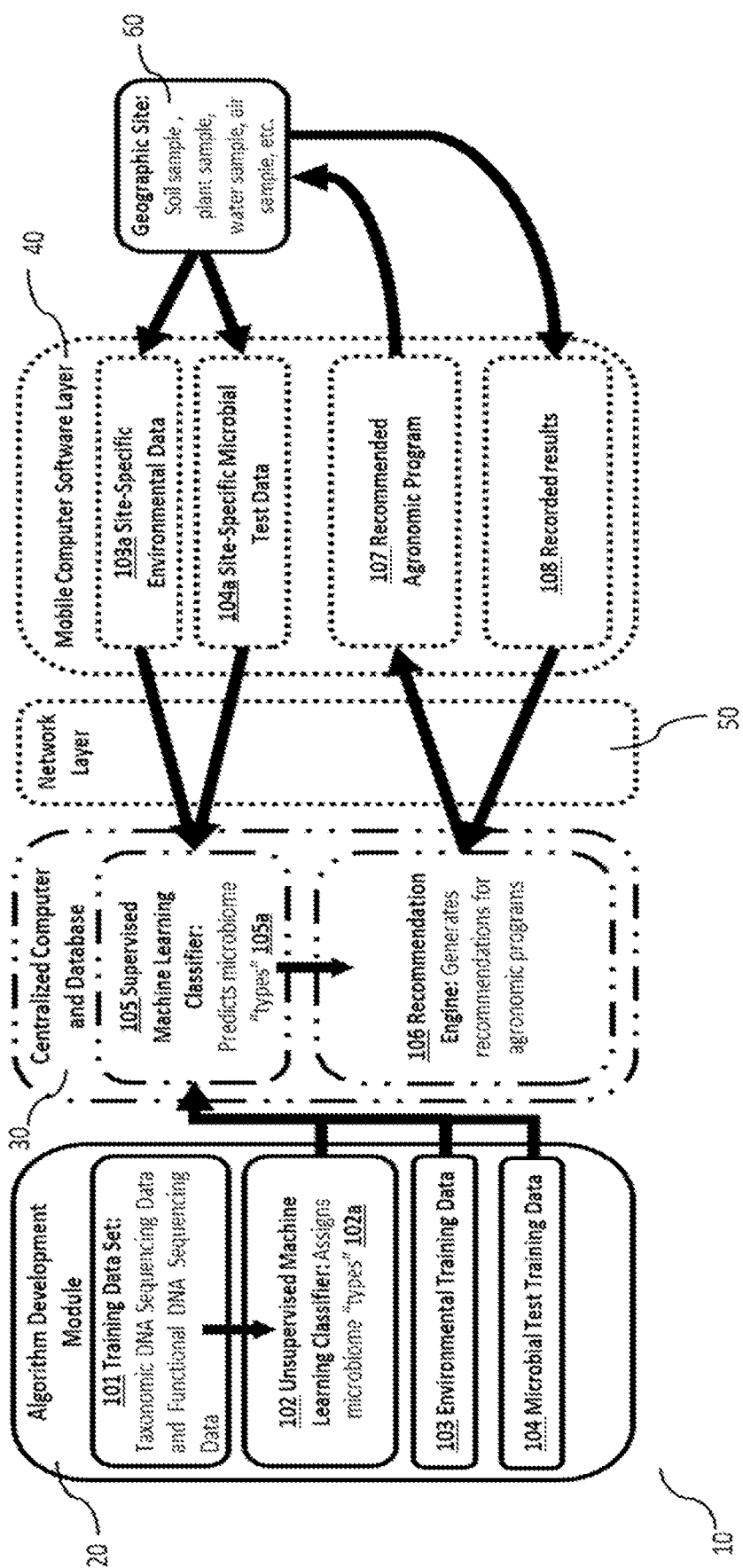
FIG. 1 is a block diagram illustrating components of a computer-implemented method according to an embodiment of the subject invention.

The subject invention provides systems and methods for classifying the microbiome(s) at a geographic site where agricultural activity is, or will be, conducted in order to, for example, improve and/or promote agricultural productivity at the site. In some embodiments, computer-implemented approaches are provided for developing one or more predictive models that analyze environmental information and DNA sequencing data from soil, plant, water and/or air samples at geographic sites in order to characterize the relationships between environment and the characteristics of the microbiome(s) present in the site's soil, plants, water and/or air.

More specifically, the subject invention utilizes a large sample set of diverse DNA sequencing input data, as well as environmental and microbial test information, to determine relationships between environmental factors and the identities, quantities and distributions of microbial species, taxonomies, gene functions and/or groupings thereof, at a chosen site. Machine learning and/or artificial intelligence classifier tools use this information to generate various output data, such as, for example, recommendations for customized formulations of soil and/or crop treatment compositions, application rate and/or timing for customized product compositions, fungicide/pesticide application rate and/or timing, irrigation practices, and/or other agricultural activity, to enhance plant health and crop productivity at the site.

Selected Definitions

The subject invention provides "microbe-based compositions," meaning a composition that comprises components that were produced as the result of the growth of microorganisms or other cell cultures. Thus, the microbe-based composition may comprise the microbes themselves and/or by-products of microbial growth. The microbes may be in a vegetative state, in spore or conidia form, in hyphae form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In preferred embodiments, the microbes are present, with growth medium in which they were grown, in the microbe-based composition. The microbes may be present at, for example, a concentration of at least $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ or $1 \times 10^{13}$ or more CFU per gram or per ml of the composition.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, an "abiotic stressor" is a non-living condition that has a negative impact on a living organism in a specific environment. The abiotic stressor must influence the environment beyond its normal range of variation to adversely affect the population performance or individual physiology of the organism in a significant way. Examples of abiotic stressors include, but are not limited to, drought, extreme temperatures (high or low), flood, high winds, natural disasters (e.g., hurricanes, avalanches, tornadoes), soil pH changes, high radiation, compaction of soil, pollution, and others. Alternatively, a "biotic stressor" is damaging and/or harmful action towards a living organism by another living organism. Biotic stressors can include, for example, damage and/or disease caused by a pest, competition with other organisms for resources and/or space, and various human activities.

As used herein, "agriculture" means the cultivation and breeding of plants, algae and/or fungi for food, fiber, biofuel, medicines, cosmetics, supplements, ornamental purposes and other uses. According to the subject invention, agriculture can also include horticulture, agronomy, landscaping, gardening, plant conservation, orcharding and arboriculture. Accordingly, agricultural/agronomic "activity" or "practices" means any action(s) related to agriculture performed by a farmer or grower at a geographic site, including, for example, tilling, plowing, mowing, planting, irrigation, fertilization, pesticide application, harvesting, and controlled burns.

As used herein, a "biofilm" is a complex aggregate of microorganisms, wherein the cells adhere to each other and/or to a surface using an extracellular polysaccharide matrix. The cells in biofilms are physiologically distinct from planktonic cells of the same organism, which are single cells that can float or swim in liquid medium.

As used herein, the term "control" used in reference to a pest means killing, disabling, immobilizing, or reducing population numbers of a pest, or otherwise rendering the pest substantially incapable of causing harm.

As used herein, the term "database" refers to either a body of data, a relational database management system (RDBMS), or both. A database may comprise any collection of data including hierarchical databases, relational databases, flat file databases, and any other structured collection of records or data that is stored in a computing system. Examples of RDBMS's include, but are not limited to, ORACLE, MYSQL, IBM, DB2, Microsoft, SQL Server, SYBASE, and POSTGRESQL databases. However, any database may be used that enables the systems and methods described herein.

As used herein, "enhancing" means improving or increasing. For example, enhanced plant health means improving the plant's ability grow and thrive; enhanced plant growth means increasing the plant's growth rate and/or biomass; and enhanced yield means increasing the number and/or marketable value of end products produced by a plant or a crop, for example, by increasing the number of fruits per plant, increasing the size and/or weight of the fruits, and/or improving the quality of the fruits (e.g., taste, texture, sweetness).

As used herein, a "geographic site" means an area of space at a location on the earth that comprises a medium in which plants can grow (e.g., soil, water, sand, sphagnum peat moss, perlite, and/or vermiculite). Geographic sites can be represented by GPS coordinates, and can include, for example, fields, plots, lots, plats, pastures, paddies, lawns, farm lands, orchards, groves, hydroponic systems, or other areas where agricultural activity is, or will be, conducted.

As used herein, "harvested" in the context of fermentation of a microbe-based composition refers to removing some or all of the microbe-based composition from a growth vessel.

As used herein, an "isolated" or "purified" compound is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

"Isolated" in the context of a microbial strain means that the strain is removed from the environment in which it exists in nature. Thus, the isolated strain may exist as, for example, a biologically pure culture, or as spores (or other forms of the strain) in association with a carrier. As used herein, a "biologically pure culture" is a culture that has been isolated from materials with which it is associated in nature. In a preferred embodiment, the culture has been isolated from all other living cells. In further preferred embodiments, the biologically pure culture has advantageous characteristics compared to a culture of the same microbe as it exists in nature. The advantageous characteristics can be, for example, enhanced production of one or more growth by-products.

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. Examples of metabolites include, but are not limited to, biosurfactants, biopolymers, enzymes, acids, solvents, alcohols, proteins, vitamins, minerals, microelements, and amino acids.

As used herein, a "microbiome" means a community of microorganisms that inhabit a sample. The "characteristics" of a microbiome include, but are not limited to, the identities, quantities and distributions of the microbial species, taxonomies, and/or groupings thereof, as well as gene functions that the microbes are capable of performing, e.g., photosynthesis and/or nitrification. A "soil microbiome" means the community of microorganisms that inhabit the soil (rhizosphere) and the subsurface plant parts growing in the soil.

As used herein, "surfactant" refers to a compound that lowers the surface tension (or interfacial tension) between two liquids or between a liquid and a solid. Surfactants act as, e.g., detergents, wetting agents, emulsifiers, foaming agents, and dispersants. A "biosurfactant" is a surfactant produced by a living organism.

As used herein, a "pest" is any organism, other than a human, that is destructive, deleterious and/or detrimental to humans or human concerns (e.g., agriculture). Pests may cause, and/or carry agents that cause, infections, infestations and/or disease. Pests may be single- or multi-cellular organisms, including but not limited to, viruses, fungi, bacteria, parasites, protozoa, arthropods and/or nematodes.

As used herein, "prevention" means avoiding, delaying, forestalling, or minimizing the onset or progression of a situation or occurrence. Prevention can include, but does not require, absolute or complete prevention, meaning the situation or occurrence may still develop, but at a later time and/or with lesser severity than without preventative measures. Prevention can include reducing the severity or extent of the onset of a situation or occurrence, and/or inhibiting the progression of the situation or occurrence to one that is more severe or extensive.

Ranges provided herein are understood to be shorthand for all of the values within the range. For example, a range of 1 to 20 is understood to include any number, combination of numbers, or sub-range from the group consisting of 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduction" refers to a negative alteration, and the term "increase" refers to a positive alteration, each of at least 1%, 5%, 10%, 25%, 50%, 75%, or 100%. As used herein, "modulate" means to cause an alteration (e.g., increase or decrease).

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially" of the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Methods and Systems for Classifying a Microbiome

The subject invention provides systems and methods for classifying the microbiome(s) at a geographic site where agricultural activity is, or will be, conducted in order to, for example, improve and/or promote agricultural productivity at the site. In certain embodiments, improving and/or promoting agricultural productivity means increasing the overall agricultural output of a geographic site, as measured by, for example, yield, quality and/or economic gain, over one or more growing seasons.

In some embodiments, computer-implemented approaches are provided for developing one or more predictive models that analyze environmental information and DNA sequencing data from geographic sites in order to characterize the relationships between environment and the characteristics of the soil, plant, water and/or air microbiome(s).

More specifically, the subject invention utilizes a large sample set of diverse DNA sequencing input data, as well as environmental and microbial test information, to determine relationships between environmental factors and the identities, quantities and distributions of microbial species, taxonomies, gene functions and/or groupings thereof, at a chosen site. Machine learning and/or artificial intelligence classifier tools use this information to generate various output data, such as, for example, recommendations for customized formulations of soil and/or crop treatment compositions, application rate and/or timing for customized product compositions, fungicide/pesticide application rate and/or timing, irrigation practices, and/or other agricultural activity, to enhance plant health and crop productivity at the site.

Advantageously, in some embodiments, the subject methods allow for assessing the characteristics of a geographic site without the need for physical sampling at the site, and also without the need for expensive classification utilizing DNA sequencing methods. Thus, the process results in a broad and generalized, yet meaningful, dataset using a significantly lower cost methodology. In certain embodiments, however, sampling and/or microbial testing methodologies, such as DNA sequencing, immuno-based testing, or culturing, may be utilized.

In general, a computer system comprising a plurality of elements and modules, receives input data from soil, plant, water and/or air samples from a plurality of geographic sites to build a classification model and a predictive classification model, and generates output data (or "recommendations") from site-specific input data, wherein the output data is used by a farmer or grower (i.e., the "user") to alter the soil, plant, water and/or air microbiome(s) in a variety of ways to achieve one or more agronomic goals. These goals can include, but are not limited to, improving yields, improving plant tolerance to abiotic and biotic stressors, minimizing the impact of plant diseases on crops, and others that are directed towards promoting agricultural productivity.

Additional features and advantages of the invention will be apparent from the following description, and from the claims.

1. Computer System

In preferred embodiments, the methods of the subject invention are implemented using a computer system, or "Microbiome Classifier System" (MCS), comprising a plurality of elements, modules, models, and/or layers.

In some embodiments, an external data server computer is communicatively coupled to the MCS, and is programmed or configured to send external data, e.g., input data, to the MCS via a network or networks. In some embodiments, the external data server is a mobile computing device, such as, for example, a smart phone.

The external data server may be owned or operated by the same entity or person as the MCS, or by a different entity or person, such as a government agency, a non-governmental organization, a non-profit organization, and/or a private data service provider.

The network or networks through which data is transferred can comprise any combination of one or more data communication networks including local area networks, wide area networks, internetworks or internets, using a wireline or wireless link, including terrestrial or satellite links. The network(s) may be implemented by any medium or mechanism that provides for the exchange of data between the various elements of the computing system.

The MCS may obtain or ingest data under user control, on a mass basis from a large number of contributors who have contributed data to a shared database system. This form of obtaining data may be termed "manual data ingest" as one or more user-controlled computer operations are requested or triggered to obtain data for use by the system.

The input data received by the MCS can include, for example, soil and/or plant metagenomic data, DNA sequencing data, environmental data, as well as other agronomic data collected from a plurality of geographic sites. In one embodiment, the external data server comprises a plurality of servers hosted by different entities. For example, a first server may contain environmental data while a second server may include metagenomic data. Additionally, environmental data may be stored in multiple servers. For example, one server may store data representing percentage of sand, silt, and clay in the soil while a second server may store data representing percentage of organic matter in the soil.

In one embodiment, the MCS is connected to a site manager computing device at a geographic site or associated with a site. The site manager computing device is programmed or configured to send and/or receive input data to/from the other elements of the MCS via the one or more networks.

The site manager computing device broadly represents one or more of a smart phone, PDA, tablet computing device, laptop computer, desktop computer, workstation, or any other computing device capable of transmitting and receiving information and performing the functions described herein. The site manager computing device may communicate via a network using a mobile application, and in some embodiments, the device may be coupled using a cable or connector to the sensor and/or controller. A particular user may own, operate or possess and use, in connection with the system, more than one site manager computing device at a time.

In certain embodiments, the site manager computing device is configured with an operating system and one or more application programs, or apps, through which a user interacts with the device and/or other elements of the MCS. The device may also interoperate with the other elements of the MCS independently and automatically under program control or logical control and direct user interaction is not always required.

In certain embodiments, the site manager computing device is connected to one or more remote sensors that are programmed or configured to produce one or more observations to be translated into input data for the MCS. The sensors may be air sensors, light sensors, temperature sensors, wind sensors, water sensors, aerial sensors, satellites, vehicle sensors, planting equipment sensors, tillage sensors, fertilizer or insecticide application sensors (chemical sensors), harvester sensors, microbe sensors and any other implement capable of receiving data from a geographic site.

The MCS may be configured to host, use or execute one or more computer programs, other software elements, digitally programmed logic, or any combination thereof to perform translation and storage of data values, construction of digital models of one or more soil, plant, water and/or air microbiomes at one or more geographic sites, generation of predictions, recommendations and notifications, and generation and sending of scripts to an application controller.

In one embodiment, the MCS is programmed with or comprises various layers, such as, for example, a communication layer, presentation layer, data management layer, hardware/virtualization layer, and/or model and data repository. A "layer" in this context means any combination of electronic digital interface circuits, microcontrollers, firmware, such as drivers, and/or computer programs or other software elements.

The communication layer may be programmed or configured to perform input/output interfacing functions, including sending requests to the external data server for input data. The communication layer may be programmed or configured to send the received data to the model and data repository to be stored. The communication layer may comprise a mobile computer software layer to perform these functions.

The presentation layer may be programmed or configured to generate a graphical user interface (GUI) to be displayed on the computer system or other computers that are coupled to the system through the network(s). The GUI may comprise controls for inputting data to be sent and/or received, generating requests for models, predictions and/or recommendations, and/or displaying models, predictions, recommendations, notifications and/or other external data.

The data management layer may be programmed or configured to manage read operations and write operations involving a repository and other functional elements of the system, including queries and result sets communicated between the functional elements of the system and the repository. Examples of data management layers include JDBC, SQL server interface code, and/or HADOOP interface code, among others. The repository may comprise a database.

When input data is not provided directly to the MCS via the external data server, the user may be prompted via one or more user interfaces on a user device (e.g., mobile computing device) to input such information. In certain embodiments, models and/or data are stored in a repository so the user and/or other users may access the data at any time. In certain, embodiments, certain elements of the input data can be predicted utilizing machine learning methodologies and other input data that is provided.

In an exemplary embodiment, the user may record environmental data from sensors, physical observation, physical sampling and testing, and/or crowd-sourced observations. Crowd-sourced observations may be provided from multiple sources, such as for example growers, farmers, land owners, equipment operators, crop advisors or consultants, and any other responsible entities. Crowd-sourced observations may be provided via oral or written reports, or electronically using mobile telephony devices or tablet computers, or any other computing devices that incorporate software tools such as mobile applications for accessing and using social media feeds.

Weather and/or climate data may be obtained from numerical weather prediction models (NWP) and/or surface networks, weather radar and satellite data, as well as "mesoscale" NWP models developed from data collected from real-time feeds to global and localized observation resources. Examples of NWP models at least include RUC (Rapid Update Cycle), WRF (Weather Research and Forecasting Model), GFS (Global Forecast System) and GEM (Global Environmental Model). Meteorological data can be received in real-time, and may come from several different NWP sources, such as from the European Centre for Medium-Range Weather Forecasting (ECMWF), Meteorological Services of Canada's (MSC) Canadian Meteorological Centre (CMC), as well as the National Oceanic and Atmospheric Administration's (NOAA) Environmental Modeling Center (EMC), and many others.

As a further example, soil information may be imported from one or more external database collections, such as for example the USDA, NRCS Soil Survey Geographic (SSURGO) dataset, containing background soil information as collected by the National Cooperative Soil Survey, or from one or more models configured to profile soil structure and composition. Soil information may also be provided from growers or landowners themselves (or other responsible entities), from soil advisory tools, from farm equipment operating in a field, and any other source of such information.

In another exemplary embodiment, a user may manually input soil, plant, water and/or air microbiome characteristics that were obtained physically by the user or another user at a geographic site of interest using, for example, culturing, immune-based assays, and DNA sequencing and amplification methods.

The hardware/virtualization layer can comprise one or more central processing units (CPUs), memory controllers, and other devices, components, or elements of a computer system such as volatile or non-volatile memory, non-volatile storage, such as disk, and I/O devices or interfaces. This layer also may comprise programmed instructions that are configured to support virtualization, containerization, or other technologies.

Embodiments of the subject computer system may use thousands or millions of different mobile computing devices associated with different users. Further, the system and/or external data server may be implemented using two or more processors, cores, clusters, or instances of physical machines or virtual machines, configured in a discrete location or co-located with other elements in a datacenter, shared computing facility or cloud computing facility. In some embodiments, the external data server may actually be incorporated within the system.

In one embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein.

In one embodiment, a mobile application ("app") is provided comprising an integrated software platform that allows a user to make fact-based decisions for their operation because it compiles historical and real-time data depicting relationships between environmental factors and soil, plant, water and/or air microbiome characteristics. The combinations and comparisons may be performed in real time and are based upon scientific models that provide potential scenarios to permit the grower to make better, more informed decisions.

Sets of instructions in the main memory of the computer system are enacted when an app is loaded for execution. The instructions can be stored in, for example, RAM or other main memory, or one or more blocks of disk storage or other non-volatile storage. In one embodiment, the app comprises, for example, instructions for receiving, translating, and ingesting input data via manual upload, external application programming interfaces (APIs) that push data to the app, or instructions that call APIs of external systems to pull data into the app.

In one embodiment, the app comprises digital map instructions comprising field map data layers stored in device memory that are programmed with data visualization tools and geospatial field notes. In one embodiment, the app comprises weather instructions to provide site-specific recent and current weather data, as well as forecasted weather information. In one embodiment, the app comprises prediction instructions programmed to provide predictions using data trends for evaluation, insights and decisions about the microbiome at a specific site upon which a grower conducts, or wants to conduct, agricultural activity.

This app can help a grower seek improved outcomes through fact-based conclusions about why, e.g., plant health was at prior levels, and insight into yield-limiting factors. These instructions may be programmed to communicate via the network(s) to back-end databases and/or analytics programs executed at the external data server computer and/or MCS and configured to analyze current environmental factors at the specific site. Programmed reports and analysis may include prescriptions for soil treatments, yield variability analysis, benchmarking of yield, and other metrics against other growers based on anonymized data collected from many geographic sites.

Applications having instructions configured in this way may be implemented for different computing device platforms while retaining the same general user interface appearance. For example, the mobile application may be programmed for execution on tablets, smartphones, or server computers that are accessed using browsers at client computers.

According to one embodiment, the methods described herein are implemented by one or more special-purpose computing devices. The special-purpose computing devices may be hard-wired to perform the methods, or may include digital electronic devices such as one or more application-specific integrated circuits (ASICs) or field programmable gate arrays (FPGAs) that are persistently programmed to perform the methods, or may include one or more general purpose hardware processors programmed to perform the methods pursuant to program instructions in firmware, memory, other storage, or a combination. Such special-purpose computing devices may also combine custom hard-wired logic, ASICs, or FPGAs with custom programming to accomplish the methods. The special-purpose computing devices may be desktop computer systems, portable computer systems, handheld devices, networking devices or any other device that incorporates hard-wired and/or program logic to implement the techniques.

For example the computing device can include a bus or other communication mechanism for communicating information; a hardware processor (e.g., a general purpose microprocessor) coupled with the bus for processing information; a main memory, such as a random access memory (RAM) or other dynamic storage device, coupled to the bus for storing information and instructions to be executed by the processor; a read-only memory (ROM) or other static storage device coupled to the bus for storing static information and instructions for processor; and/or a storage device, such as a magnetic disk, optical disk, or solid-state drive coupled to the bus for storing information and instructions.

The computing device may also comprise a display, such as monitor, for displaying information to a computer user; and/or an input device (e.g., alphanumeric and other keys, cursor control, such as a mouse, a trackball, or cursor direction keys) coupled to the bus for communicating information and command selections to the processor.

The computing device may further utilize hard-wired logic, one or more ASICs of FPGAs, firmware and/or program logic to implement the methods described herein, which, in combination with the computer system, causes or programs the entire system to be a special-purpose machine.

According to one embodiment, the methods described herein are performed by the MCS in response to the processor executing one or more sequences of one or more instructions contained in the main memory. Such instructions may be read into the main memory from another storage medium, such as a storage device. Execution of the sequences of instructions contained in the main memory causes the processor to perform the process steps described herein. In alternative embodiments, hard-wired circuitry may be used in place of or in combination with software instructions.

The computer system can also include a communication interface coupled to the bus. The communication interface provides a two-way data communication coupling to a network link that is connected to a local network. For example, the communication interface may be an integrated services digital network (ISDN) card, cable modem, satellite modem, or a modem to provide a data communication connection to a corresponding type of telephone line. As another example, communication interface may be a local area network (LAN) card to provide a data communication connection to a compatible LAN. Wireless links may also be implemented. In any such implementation, the communication interface sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the Internet. Local network and Internet both use electrical, electromagnetic or optical signals that carry digital data streams. The signals through the various networks and the signals on network link and through communication interface, which carry the digital data to and from computer system, are example forms of transmission media.

The MCS can send messages and receive data, including program code, through the network(s), network link and communication interface. The received code may be executed by the processor as it is received, and/or stored in the storage device, or other non-volatile storage for later execution.

2. Function of Computer System

A user can carry out a process for generating output data that is useful for classifying the soil, plant, water and/or air microbiome(s) at a geographic site using the computer system described. In some embodiments, the MCS is utilized for classifying the microbiome(s) at a geographic site in order to produce recommendations for agronomic programs that will improve soil-crop interaction. In some embodiments, the methods are used for classifying the microbiome by taxonomy, for example, to identify the distributions and/or quantities of species and/or taxonomies of microorganisms in soil, plant, water and/or air samples. In some embodiments, the methods are used for classifying the microbiome by representative gene functions, such as nutrient fixation, photosynthesis, and/or production of certain metabolites.

Figure 2:
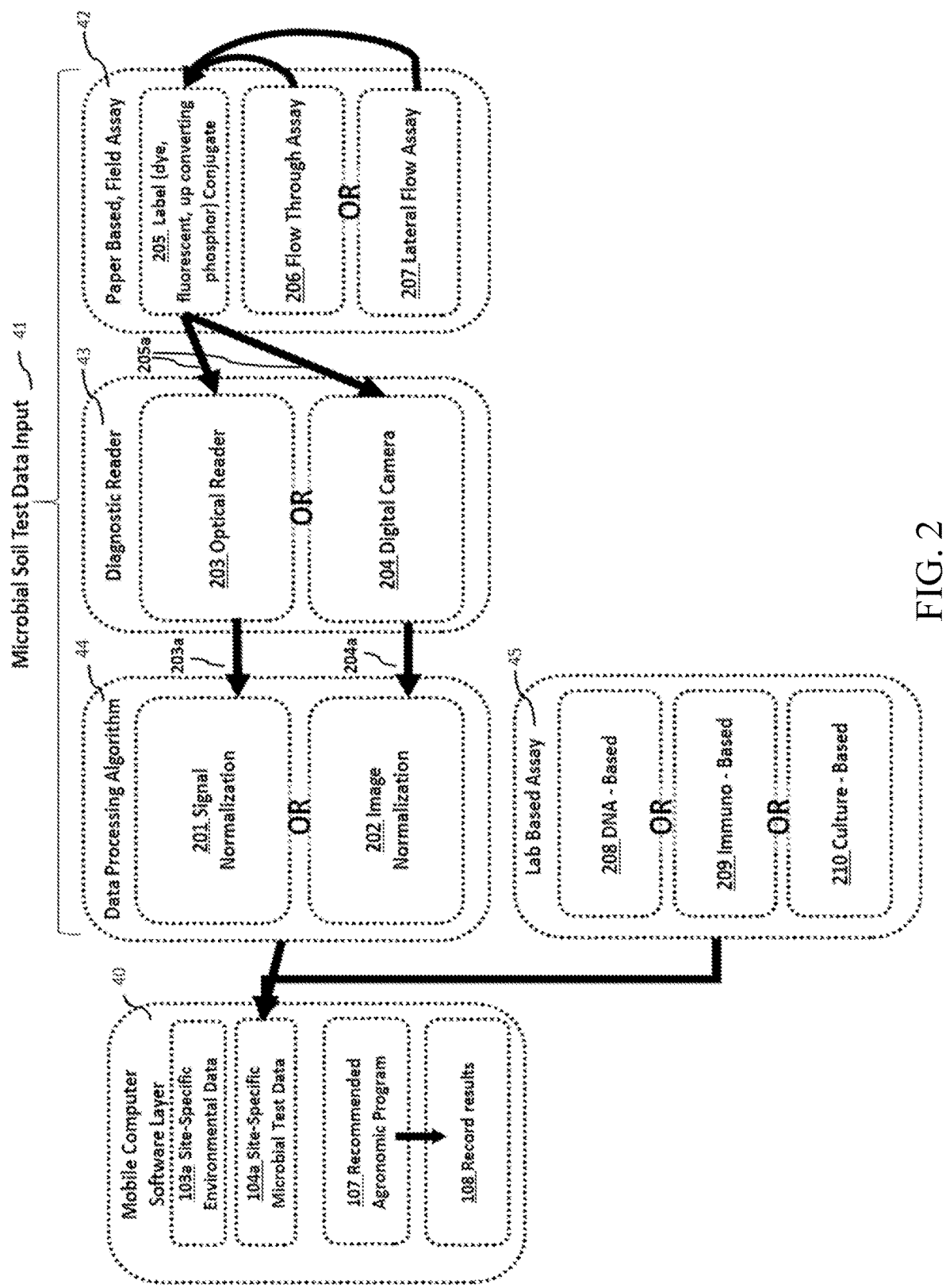
FIG. 2 is a block diagram illustrating computer implemented methods for obtaining microbial test data for inputting into a computer system according to an embodiment of the subject invention.
Figure 3:
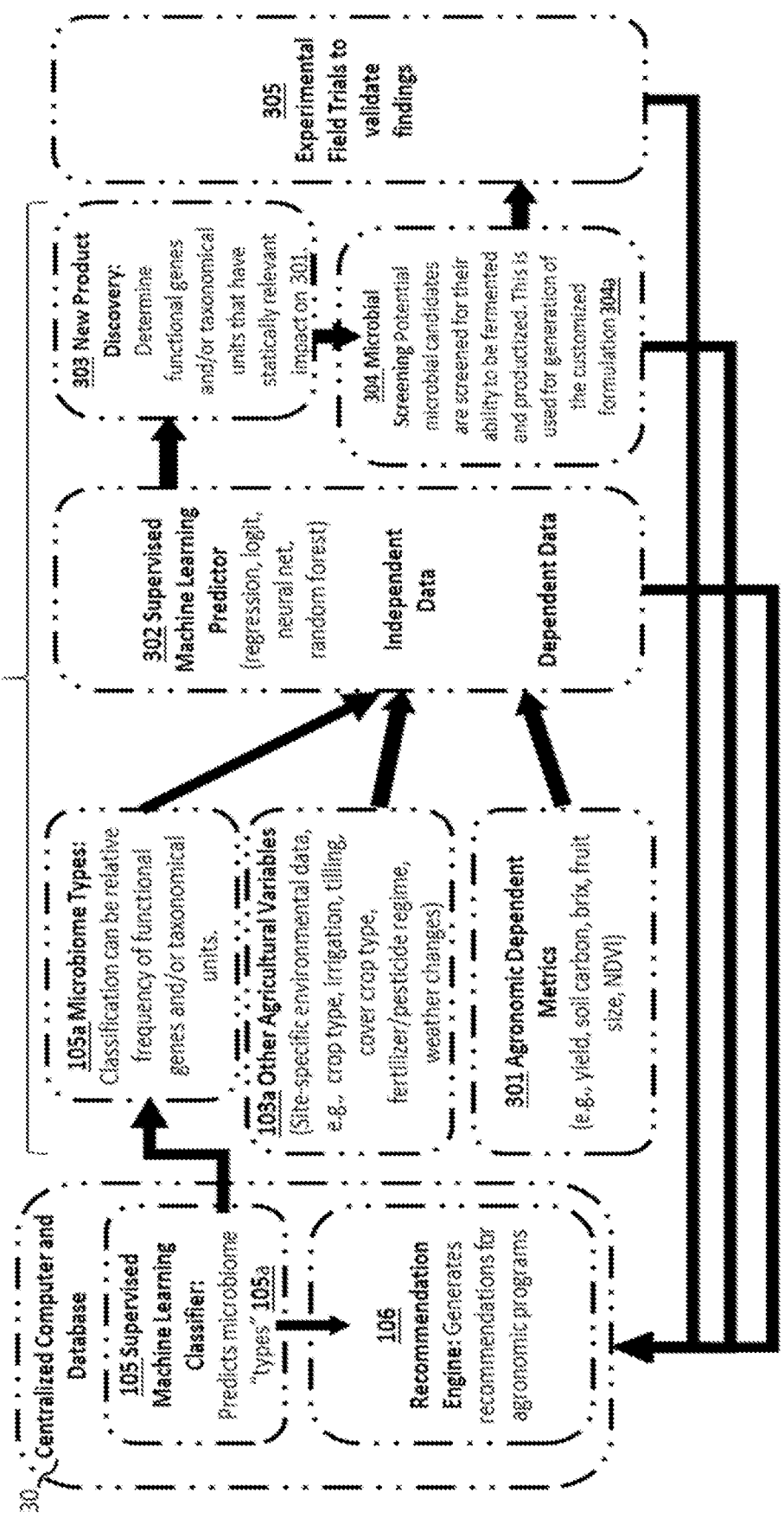
FIG. 3 is a flow diagram illustrating the steps for developing the Recommendation Engine according to one embodiment of the subject invention.

FIGS. 1-3 show block/flow diagrams that depict non-limiting examples of the components and implementation of the MCS 10 according to the subject invention, as it is used to generate recommendations for agronomic programs 107 at a specific geographic site 60. FIG. 4 shows a visual representation of microbiome "types" as generated by the subject invention. The scope of the invention is not intended to be limited to only the elements listed in the figures. Numerous other elements can be included that are not specifically included in FIGS. 1-4. Additionally, FIGS. 2-4 are described in connection with certain elements of FIG. 1; however, other embodiments of FIG. 1 may be practiced in many other contexts and references herein to units of FIGS. 2-4 are merely examples that are not intended to limit the broader scope of FIG. 1.

The MCS 10 can comprise numerous elements, layers, models and/or modules, including, for example, an Algorithm Development (AD) module 20, an unsupervised machine learning classifier ("UMLC") tool 102, a supervised machine learning classifier ("SMLC") tool 105, and a Recommendation Engine 106, which function together for generating output data. Output data may take many different forms, including, for example, various predictions and/or recommendations.

In one embodiment, the MCS 10 comprises an Algorithm Development ("AD") module 20 for developing a "microbiome classification model." The MCS 10 can comprise a data ingest module for receiving, requesting, or otherwise obtaining and ingesting input data from an external data server, a mobile computing device, a site manager computing device and/or from manual input by a user.

In one embodiment, the data ingest module receives a Training Data Set 101, which is input data used for "training" an unsupervised machine learning classifier tool 102. In certain embodiments, the Training Data Set 101 comprises broad DNA sequencing data derived from samples taken from a plurality of geographic sites.

The DNA sequencing data can comprise "taxonomic DNA sequencing data," or sequencing data obtained from 16s and/or Internal Transcribed Spacer (ITS) sequencing of bacterial and fungal species, respectively. These data target a specific region of species' genomes, thus providing specific taxonomic-identifying information.

The DNA sequencing data can also comprise "functional DNA sequencing data," or metagenomic data. As used herein, "metagenomic data" means, in general, data obtained from direct genetic analysis of the entire genomes of living organisms contained in an environmental sample. In certain embodiments, the analysis is performed using shotgun sequencing. The functional DNA sequencing data provide gene function-identifying information.

The Training Data Set 101 can reveal the characteristics of the microbiome(s) at a site by, for example, providing relative frequencies of taxonomic-indicating and/or function-indicating gene markers in the samples. Samples according to the subject invention can include, for example, soil, plant, water and/or air samples. In certain specific embodiments, the samples are soil samples.

In some embodiments, the Training Data Set 101 is obtained from a crowd-sourced database that houses and classifies the DNA sequencing and/or other identification results from individual samples collected from a plurality of geographic sites around the world. For example, the Earth Microbiome Project is one such database (www.earthmicrobiome.org).

In some embodiments, the Training Data Set 101 is obtained from another source, such as licensed metagenomic test data from another private entity and/or from sampling and analysis performed by the user or another person or entity.

In preferred embodiments, the AD module 20 produces a "microbiome classification model" based on the relative frequencies of taxonomic- and/or function-indicator gene markers from each sample.

The term "model" in this context, refers to an electronic digitally stored set of executable instructions or algorithms, and data values, associated with one another, that are capable of receiving and responding to a programmatic or other digital call, invocation, or request for resolution based upon specified input values, to yield one or more stored output values that can serve as the basis of computer-implemented predictions and/or recommendations, output data displays, or machine control, among other things. The skilled artisan may find it convenient to express models using mathematical equations, but that form of expression does not confine the models disclosed herein to abstract concepts; instead each model herein has a practical application in a computer in the form of stored executable instructions and data that implement the model using the computer. The model data may include, for example, a model of past events at the one or more geographical sites, a model of the current status of the one or more geographical sites, and/or a model of predicted events at the one or more geographic sites.

In certain embodiments, the microbiome classification model is used by a machine learning classifier to analyze the Training Data Set 101. The term "classifier," as used herein, refers to a model, algorithm, program, or other set of instructions that are capable of grouping data points based on similarities between them.

In one embodiment, a machine learning tool is used as a classifier. Many different types of machine learning and/or artificial intelligence may be utilized as classifiers according to the subject invention. The machine learning may be supervised or unsupervised. It may apply techniques that include, but are not limited to, k-nearest neighbor (KNN), k-means, logistic regression, logit, random forest, support vector machines or networks (SVM), and one or more neural networks. In one embodiment, the MCS 10 utilizes more than one machine learning tool.

In preferred embodiments, an unsupervised machine learning classifier ("UMLC") 102 analyzes the Training Data Set 101. "Unsupervised" machine learning follows principles of self-organization, where algorithms are left to identify input data patterns and organize the data according to those patterns.

Unsupervised learning can utilize clustering, where inherent groupings in the data are identified by organizing data based on shared characteristics. Instead of responding to feedback, cluster analysis identifies shared characteristics and classifies each new data point based on the presence or absence of that characteristic. In some embodiments, the UMLC uses clustering techniques such as, for example, k-means and/or KNN. Unsupervised learning can also utilize association rule learning, where broader rules are identified that describe, or associate, portions of the data with one another.

In the subject system, using the microbiome classification model, the UMLC clusters, or classifies, samples into "microbiome types" 102a based on similarities between microbiome characteristics in the samples.

Microbiome characteristics that can be used for classification include, for example, identities, quantities and/or distributions of microbial species and/or taxonomies in a sample; relative frequencies of species- and/or taxonomic-indicating genetic markers; and/or identification and/or groupings of microbial species and/or taxonomies based on the prevalence of specific gene functions, e.g., capabilities for nitrification and/or photosynthesis.

In one embodiment, the AD module 20 next receives (e.g., through the data ingest module) one or more other agronomic training data sets from the plurality of geographic sites from where the Training Data Set 101 was collected. In one embodiment, the other agronomic training data sets comprise "environmental" training data 103.

As used herein, "environmental" data (whether "training data" 103 or "site-specific" 103a) comprises any condition or factor that characterizes or acts upon a geographic site, whether in the past, present or forecast. In some embodiments, the environmental data is obtained from one or more databases housing crowd-sourced information. In certain embodiments, non-numerical environmental data are assigned a value, e.g., a numerical value or a characteristic value, to serve as an individual data point in the computer system.

Non-limiting examples of environmental data for a geographic site include:

(a) location (e.g., GPS coordinates, climate zone, elevation, site area and measurements);

(b) weather and/or climate averages and/or patterns (e.g., precipitation, temperature, wind, forecast, pressure, visibility, cloud coverage, heat index, UV index, dew point, humidity, snow depth, air quality, sunrise, and/or sunset), as well as calculated phenologic metrics derived therefrom (e.g., growing degree days, cooling degree days, heating degree days);

(c) soil horizon data, including number of horizons; type(s) of soil in each horizon (e.g., clay, sandy clay, silty clay, clay loam, silty clam loam, sandy clay loam, loam, sandy, sandy loam, silty loam, and silty);

composition of soil each horizon (e.g., pH, humus, salts, enzymes, minerals and other elements and/or nutrients, clays, carbonates, sesquioxides, water, ice, microbial constituents, concentrations, and absolute quantities);

physical characteristics of each horizon (e.g., depth, thickness, color, electrical conductivity, texture, hardness, cementation, amount of respiration, and/or any other characteristic described in, e.g., the USDA Field Book for Describing and Sampling Soils (2012)); and/or classification(s) of each horizon (e.g., diagnostic horizons from the World Reference Base for Soil Resources, including: Anthraquic, Argic, Calcic, Cambic, Chernic, Cryic, Duric, Ferralic, Ferric, Folic, Fragic, Fulvic, Gypsic, Histic, Hortic, Hydragric, Irragric, Melanic, Mollic, Natric, Nitic, Petrocalcic, Petroduric, Petrogypsic, Petroplinthic, Pisoplinthic, Plaggic, Plinthic, Pretic, Protovertic, Salic, Sombric, Spodic, Terric, Thionic, Umbric, and Vertic horizons; and USDA soil taxonomy diagnostic horizons, epipedons and/or layers, including: Anthropic, Folistic, Histic, Melanie, Mollie, Ochric, Plaggen, Umbric, Agric, Albic, Anhydric, Argillic, Calcic, Cambic, Duripan, Fragipan, Glossic, Gypsic, Kandic, Natric, Nitic, Ortstein, Oxic, Petrocalcic, Petrogypsic, Petroplinthic, Placic, Salic, Sombric, and Spodic);

(d) crop data (e.g., type of plant(s) grown in the past or present, type of plant(s) to be grown, date of planting, date of harvest, planting density, number of plants in a crop, harvest size, and/or marketable yield from harvest);

(e) agricultural supplementation and irrigation practices (e.g., fertilizer use, pesticide use, herbicide use, tilling, soil transplantation/supplementation/amendment, water source), as well as methods of application, volumes of application, and timing of application;

(f) crop imagery and/or diagnostic data (e.g., imagery and/or light spectrum information from a sensor, camera, computer, smartphone, tablet, UAV, plane, or satellite);

(g) historical non-agricultural land activity, including anthropogenic activity (e.g., building and/or development, plowing, mining, drilling, oil and gas recovery, dumping, remediation, toxic waste deposit, livestock grazing) and natural occurrences (e.g., flooding, landslides, earthquakes, sinkholes, avalanches, and fires); and (h) other site characteristics, including pest populations, invasive and non-invasive flora and fauna populations, bodies of water, and natural and/or man-made landmarks.

In certain preferred embodiments, environmental data 103, 103a includes soil data (e.g., soil type(s), soil characteristics, soil composition) and crop data (e.g., past, present and/or desired crop type(s)).

In one embodiment, the other agronomic training data sets comprise "microbial test" training data 104. "Microbial test data" (whether "training data" 104 or "site-specific" 104a) can include, for example, quantitative test results for indicator gene-markers or species of microbes in a soil, plant, water and/or air sample, generated by lab-based 45 tests (e.g. DNA-based, immuno-based or culture-based assays) or in-field 42, 43, 44 tests, such as paper-based assays. These assays can detect, for example, DNA, antibodies, proteins, and/or other analytes indicative of the presence and/or number a particular microorganism in a sample.

Additional examples of methods and assays for detecting, quantifying and/or tracking microorganisms are disclosed in International Patent Application Pub. No. WO 2018/213604 A1, which is incorporated herein by reference in its entirety, to the extent that it does not conflict with the present disclosure.

The AD 20 then develops a supervised machine learning classifier ("SMLC") 105 based on relationships drawn between the Training Data Set 101 and the other agronomic training data 103, 104 from the plurality of geographic sites. More specifically, the SMLC 105 creates a predictive classification model, which utilizes these relationships to predict microbiome classification types 105a from samples at a specific geographic site 60.

In some embodiments, the SMLC 105 can be housed in a separate element, e.g., a Centralized Computer and Database system 30.

With "supervised" machine learning, known pairs of input data-output variables are used to train an algorithm to learn a function that maps an input to an output, and be able to predict, using an inferred function, output variables when new input data is received. Overtime, the algorithm iteratively makes predictions based on the data, thus making those prediction capabilities increasingly more accurate. Supervised learning can comprise classification, where the output variable is a category, or regression, where the output variable is a real (e.g., numerical) value.

In some embodiments; the predictive classification model may be cross-validated to ensure accuracy of the model. Cross validation may include comparison to ground truth that compares predicted results with actual results at a site, such as a comparison of a predicted microbiome classification with quantitative test results from a sample at the same location.

Thus, in certain embodiments, the relationships between the various types of input data may be identified and developed by training the SMLC 105 to continually analyze input data, to build a more comprehensive dataset that can be used to make improvements to the predictive classification model and the ability of the MCS 10 to draw automatic associations between DNA sequencing data and other agronomic data.

In specific embodiments, the SMLC 105 builds from the microbiome "types" 102a assigned by the UMLC 102 and from other agronomic training input data 103, 104, to analyze site-specific prediction input data 103a, 104a from a specific geographic site of interest 60. The SMLC 105 then predicts microbiome types 105a at the specific geographic site 60.

In certain embodiments, the site-specific prediction input data comprises agronomic data collected from the specific geographic site 60, such as, for example, site-specific environmental data 103a and/or site-specific microbial test data 104a.

In certain embodiments, the SMLC 105 can predict and/or simulate characteristics of a geographic site where certain data have not been collected, such as soil data and/or microbiome classification data, based on predictive associations. For example, known soil type can be compared with known weather data to predict the moisture retention capabilities of the soil, as well as specific species of microbes in the soil.

In preferred embodiments, the computer system 10 further comprises a Recommendation Engine 106 which correlates predicted microbiome classification (types) 105a with an optimal agronomic program 107 for a specific geographic site 60.

In some embodiments, the Recommendation Engine 106 utilizes a Supervised Machine Learning Predictor ("SMLP") 302, which identifies the statistically impactful relationships between predicted sample classification 105a, site-specific environmental data 103a, and an agronomic metric of interest (e.g., yield, soil carbon sequestration, brix value, fruit size, NDVI, etc.) 301. The SMLP 302 can then identify agricultural products that can have a statistically relevant impact on the agronomic metric of interest 301 to promote agricultural productivity.

An agronomic program can include, for example, a schedule or list of one or more agricultural activities to be conducted at a site; a customized soil and/or crop treatment composition for applying at the site; and/or specific instructions for applying treatment compositions at a site.

Following the implementation of one or more recommended agronomic programs 107 at a specific geographic site 60, the program and its results (e.g., changes in plant health, growth and/or yield) 108 can be recorded and submitted back into the Recommendation Engine 106, to validate the impact of the agronomic program 107 and further improve the recommendation capabilities of the system 10.

In certain embodiments, the models utilized by the UMLC 102, SMLC 105 and/or SMLP 302 can be developed using one or more other agronomic models that analyze one or more physical and empirical characteristics impacting, for example, soil quality and crop health at a site. Such models may include elements of crop, soil, plant, land surface, and other modeling paradigms. These models may include, for example, phenological models, such as growing degree day (GDD) models, soil modeling elements such as the EPIC, APEX, and ICBM soil models, and land surface models such as the NOAH, Mosaic, and VIC models.

It is also contemplated that the input data described herein may be applied to existing precision agriculture models, as well as to customized models developed for specific conditions at a site. More than one modeling paradigm may be employed alongside the models described herein, and the subject machine learning tools may apply elements of many models in combination with others. Therefore, the present invention is not to be limited by any one agronomic model referenced herein.

In certain embodiments, the output data generated by the Recommendation Engine 106 is further processed using a visualization module, which translates output data into visual forms, such as flow charts, soil horizon maps, and/or aerial view maps, depicting, for example, the location of microbial species, taxonomies and/or groupings thereof across the area of a site and/or as distributed throughout the soil layers.

3. Practical Applications by Users

The methods and systems of the subject invention can be used in precision agriculture for enhancing the efficiency and productivity of agriculture operations. A user can employ the computer-implemented methods to generate customized, site-specific recommendations for agronomic programs that can enhance agricultural productivity at a site.

In some embodiments, the MCS 10 is utilized for classifying the microbiome(s) at a geographic site 60 in order to produce recommendations for agronomic programs 107 that will improve, for example, soil-crop interaction.

In one embodiment, the MCS 10 recommends an agronomic program 107 that comprises a schedule or list of one or more agricultural activities that promote agricultural productivity. These can include, for example, recommendations for type of plant(s) or crop(s) to grow; type and/or amount of fertilizer to apply, and timing/mode of application; type and/or amount of pesticides, fungicides and/or herbicides to apply, and timing/mode of application; amount of water to apply and timing/mode of irrigation; and/or soil conditioning, such as tilling, applying organic material, fumigating, and/or planting cover crops.

In one embodiment, an agronomic program 107 helps improve the soil, plant, water and/or air microbiome at a geographic site. Improving a microbiome can mean altering the identities, distribution and/or numbers of individual species, taxonomies and/or groupings of organisms present in a microbiome, or otherwise altering the frequency of representative gene functions within the microbiome, in a way that promotes agricultural productivity at the site.

In certain embodiments, improving a microbiome means the microbiome is altered such the proportion of beneficial microorganisms and/or non-detrimental/commensal microorganisms is increased. In certain embodiments, improving a microbiome means altering the microbiome so that a majority (e.g., >50%) of the microorganisms are beneficial and/or non-detrimental/commensal microorganisms. This can be achieved by agricultural activities including, for example, applying beneficial and/or non-detrimental/commensal organisms to a site; applying products to a site such as prebiotics, that support and/or promote the growth of desirable microorganisms and/or pesticides that suppress the growth of detrimental microorganisms; and/or implementing other practices that support microbiome diversity, such as, for example, crop rotation, irrigation practices, and/or soil amendment application.

As used herein, a "beneficial" microbe is one that directly or indirectly confers a site-specific benefit towards promoting agricultural productivity, rather than a microbe that is merely commensal or detrimental. These benefits can include one or more of: enhancing plant health, growth and/or yields, enhancing plant immunity and tolerance to abiotic and/or biotic stressors; enhancing carbon sequestration in soil and/or reducing emissions of greenhouse gases from agricultural activity; enhancing soil nutrient bioavailability for plant roots; reducing the amount of chemical fertilizers, pesticides and/or other soil amendments required at a site; reducing water usage and runoff; reducing pest numbers and disease outbreaks; encouraging the presence and/or colonization of other beneficial above- and below-ground organisms, and increasing biodiversity.

A "commensal" microorganism is one that exists within the microbial community in a non-beneficial manner, while not necessarily causing any direct harm thereto. Commensal microorganisms can, however, be beneficial when they outcompete detrimental microorganisms for space and resources, as well as detrimental when they outcompete beneficial microorganisms.

A "detrimental" microorganism is one that causes direct or indirect harm, for example, by killing and/or parasitizing plants and/or beneficial microorganisms or producing harmful growth by-products. Detrimental microorganisms can also include pathogenic organisms that can cause disease in plants and/or animals.

In certain embodiments, the MCS 10 recommends optimum soil, plant, water and/or air microbiome characteristics for a specific geographic site 60 where, for example, a user is conducting, or wishes to conduct, agricultural activity. Thus, the optimum microbiome(s) can be thought of as a customized goal or reference template when implementing methods for improving the endemic microbiome(s) at that site and/or achieving one or more agricultural productivity goals (such as, e.g., increased yield, pest control and/or reduced water usage).

In certain embodiments, the MCS 10 predicts the microbiome type(s) at a specific geographic site 60, and the Recommendation Engine 106 recommends a specific product to be applied at the geographic site 60. For example the MCS 10 can be used to formulate a customized soil and/or crop treatment composition for applying to a plant, a crop and/or the surrounding environment (e.g., the rhizosphere) to promote agricultural productivity. The recommended formulation 304a can comprise, for example, specific substances, combinations thereof, amounts thereof, and/or proportions thereof in the composition. The recommended formulation 304a can also comprise the form in which the composition is transported and/or applied, for example, dried powder, granules, tablets, or spikes, liquid, gel, aerosol, slow-release form, concentrated or diluted form, etc.

In certain embodiments, the soil and/or crop treatment composition comprises one or more chemical, synthetic and/or inorganic substances that promote agricultural productivity. These can include, for example, mined or synthesized fertilizer components, chemical/synthetic pesticides, fungicides, and/or herbicides, and synthetic plant growth regulators.

In certain embodiments, the soil and/or crop treatment composition comprises one or more bio-based components that promote agricultural productivity. Bio-based components can include naturally-derived components, such as, for example, organic matter, plant and/or animal by-products, essential oils and/or other plant extracts, microorganisms, and/or the by-products of fermenting microorganisms.

In certain embodiments, the soil and/or crop treatment composition comprises a combination of one or more chemical, synthetic and/or inorganic substances and one or more bio-based components.

After receiving the recommendation for the customized formulation 304a, a user can then obtain and apply the soil and/or crop treatment composition. Methods for producing and applying a soil and/or crop treatment composition according to one embodiment of the subject invention are provided herein, although in certain embodiments, the Recommendation Engine 106 can also generate a recommendation providing instructions for obtaining and/or applying the composition along with the recommendation providing the customized formulation 304a. For example, a recommendation can further comprise optimal timing and/or rates of application for the product to ensure a positive impact on one or more agronomic metrics that can be influenced by the soil, plant, water and/or air microbiome(s), including, for example, enhancement of plant health and growth, crop yield, disease protection, and/or flower and fruit timing.

In certain embodiments, a user's recommended formulation 304a is then delivered to a company that specializes in production of such compositions as a request for the actual product. This can be performed automatically by the MCS 10, where the recommendation is sent as output data via network to a receiving computer owned and/or operated by the company, and then translated into an order for the customized product.

The user can also request an order from the company for the customized product via, for example, telephone, e-mail, facsimile, postal service, and/or an online order form located on the company's website. The company then manufactures the composition and transports it to the user for physical application to a geographic site 60.

4. Customized Soil and/or Crop Treatment Compositions

As used herein, a "soil treatment," "soil amendment" or "soil conditioner" is any organism, compound, material, or combination of organisms, compounds or materials that are added into soil to enhance the physical, chemical and/or biological properties of the soil. A "crop treatment" can be applied to an entire crop, including above- and below-ground plant parts, as well as to the crop plants' surrounding environment (e.g., soil), to provide a benefit to the crop and/or its environment. Accordingly, in some embodiments, a crop treatment composition can also be a soil treatment composition.

In certain embodiments, the soil and/or crop treatment composition comprises one or more chemical, synthetic and/or inorganic substances that promote agricultural productivity. These can include, for example, mined or synthesized fertilizer components (e.g., ammonium nitrate, calcium ammonium nitrate, monoammonium phosphate, diammonium phosphate, ammonium phosphate, superphosphate, calcium nitrate, urea, potassium sulfate, potassium nitrate, potassium carbonate, potassium mchloride, NPK compound fertilizers, EDTA, and/or micronutrients, such as molybdenum, zinc, boron and copper); chemical/synthetic pesticides (e.g., neonicotinoids, such as imidacloprid; organochlorines, such as DDT, toxaphene, chlordane, dieldrin, and aldrin; organophosphates, such as diazinon, glyphosphate, and malathion; carbamates, such as carbofuran, aldicarn and carbaryl; and pyrethroids, such as permethrin, fenpropanthrin, deltamethrin and cypermethrin); chemical/synthetic fungicides (e.g., chlorothalonil, thiophanate-methyl, triadimefon, and triforine); chemical/synthetic herbicides (e.g., sulfonylureas, amodosulfuron, flazasulfuron, metsulfuron-methyl, rimsulfuron, sulfometuron-methyl, terbacil, nicosulfuron, and triflusulfuron-methyl); and synthetic plant growth regulators (e.g., alar, B-9, arest, IBA, cycocel, triacontanol, brassins, xanthoxin, and batasins).

In certain embodiments, the soil and/or crop treatment composition comprises one or more bio-based components that promote agricultural productivity. Bio-based components can include, for example, organic fertilizers and/or soil amendments (e.g., manure, treated sewage, compost, seed meal, ground sea shells, blood meal, feather meal, animal hides, horns, hooves, bonemeal, peat, bark, coir, sawdust, and oil cakes); naturally-derived pesticides (e.g., neem oil, diatomaceous earth, pyrethrum, spinose, rotenone, insecticidal soap, boric acid, natural dusts, peppermint oil, clove oil, citrus oils, lavender oil, thyme oil, and rosemary oil); plant-derived plant growth regulators (e.g., auxins, gibberellins, cytokinins, ethylene, and abscisic acid); and microorganisms (e.g., bacteria, yeasts and fungi) and/or the by-products of fermenting microorganisms (e.g., fermentation broth, cell biomass, extracellular metabolites).

In certain embodiments, the soil and/or crop treatment composition comprises a combination of one or more chemical, synthetic and/or inorganic substances and one or more bio-based components.

5. Microbe-Based Soil Treatment Composition

In an exemplary embodiment, a customized soil treatment composition is provided, comprising one or more beneficial microorganisms and/or microbial growth by-products. The microorganisms can be selected from, for example, bacteria, yeasts and fungi that are capable of growing in soil, and that directly or indirectly confer one or more benefits to a site.

In preferred embodiments, the one or more microorganisms are selected based on functional genes and or taxonomic identity having a statistically relevant impact on one or more agronomic metrics of interest at a geographic site. The potential microbial candidates are then screened for their ability to be produced and converted into a product that can be transported to and used by a farmer or grower.

The composition can further comprise, for example, residual nutrients and/or growth medium used for cultivation of the one or more microorganisms; an agriculturally-acceptable carrier, such as water; added nutrients and/or prebiotics to support the growth of the one or more beneficial microorganisms; and/or any other compatible additives for enhancing plant health, such as fertilizers, herbicides, pesticides and/or soil amendments.

The microorganisms useful according to the subject invention can be, for example, non-plant-pathogenic strains of bacteria, yeast and/or fungi. These microorganisms may be natural, or genetically modified microorganisms. For example, the microorganisms may be transformed with specific genes to exhibit specific characteristics, or may have specific genes removed, e.g., via CRISPR. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In one embodiment, the microorganism is a yeast or fungus. Yeast and fungus species suitable for use according to the current invention, include *Aureobasidium* (e.g., *A. pullulans*), *Blakeslea*, *Candida* (e.g., *C. apicola*, *C. bombicola*, *C. nodaensis*), *Cryptococcus*, *Debaryomyces* (e.g., *D. hansenii*), *Entomophthora*, *Hanseniaspora*, (e.g., *H. uvarum*), *Hansenula*, *Issatchenkia*, *Kluyveromyces* (e.g., *K. phaffii*), *Mortierella*, *Mycorrhiza*, *Penicillium*, *Phycomyces*, *Pichia* (e.g., *P. anomala*, *P. guilliermondii*, *P. occidentalis*, *P. kudriavzevii*), *Pleurotus* spp. (e.g., *P. ostreatus*), *Pseudozyma* (e.g., *P. aphidis*), *Saccharomyces* (e.g., *S. boulardii sequela*, *S. cerevisiae*, *S. torula*), *Starmerella* (e.g., *S. bombicola*), *Torulopsis*, *Trichoderma* (e.g., *T. reesei*, *T. harzianum*, *T. hamatum*, *T. viride*), *Ustilago* (e.g., *U. maydis*), *Wickerhamomyces* (e.g., *W. anomalus*), *Williopsis* (e.g., *W. mrakii*), *Zygosaccharomyces* (e.g., *Z. bailii*), and others.

In certain embodiments, the microorganisms are bacteria, including Gram-positive and Gram-negative bacteria. The bacteria may be, for example *Agrobacterium* (e.g., *A. radiobacter*), *Azotobacter* (*A. vinelandii*, *A. chroococcum*), *Azospirillum* (e.g., *A. brasiliensis*), *Bacillus* (e.g., *B.*

*amyloliquefaciens, B. circulans, B. firmus, B. laterosporus, B. licheniformis, B. megaterium, Bacillus mucilaginosus, B. subtilis*), *Frateuria* (e.g., *F. aurantia*), *Microbacterium* (e.g., *M. laevaniformans*), *Myxobacteria* (e.g., *Myxococcus xanthus, Stignatella aurantiaca, Sorangium cellulosum, Minicystis rosea*), *Pantoea* (e.g., *P. agglomerans*), *Pseudomonas* (e.g., *P. aeruginosa, P. chlororaphis* subsp. *aureofaciens* (*Kluyver*), *P. putida*), *Rhizobium* spp., *Rhodospirillum* (e.g., *R. rubrum*), *Sphingomonas* (e.g., *S. paucimobilis*), and/or *Thiobacillus thiooxidans* (*Acidothiobacillus thiooxidans*).

In one embodiment, the microorganisms of the subject composition comprise about 5 to 20% of the total composition by weight, or about 8 to 15%, or about 10 to 12%. In one embodiment, the composition comprises about $1\times10^6$ to $1\times10^{12}$, $1\times10^7$ to $1\times10^{11}$, $1\times10^8$ to $1\times10^{10}$, or $1\times10^9$ CFU/ml, each, of the one or more microorganisms.

In one exemplary embodiment, the soil treatment composition can comprise from 1 to 99% by weight of a first microorganism and from 1 to 99% by weight a second microorganism. In some embodiments, the cell count ratio of the first microorganism to the second microorganism is about 1:9 to about 9:1, about 1:8 to about 8:1, about 1:7 to about 7:1, about 1:6 to about 6:1, about 1:5 to about 5:1 or about 1:4 to about 4:1.

In one exemplary embodiment, the first microorganism is a conidia-forming (spore-forming) fungal strain, and the second microorganism, is a spore-forming bacterial strain. Preferably, according to this exemplary embodiment, the first microorganism is a *Trichoderma* spp. fungus and the second microorganism is a spore-forming *Bacillus* spp. bacterium, although other combinations are envisioned. In certain embodiments, the composition comprises *Trichoderma harzianum* and *Bacillus amyloliquefaciens*.

In some embodiments, the composition can further comprise one or more additional microbes. In one embodiment, the additional microbes can comprise one or more of, for example, a *Mycobacterium* and/or other type of bacteria, a yeast and/or a fungus. In an exemplary embodiment, a *Mycobacterium* is included, wherein the *Mycobacterium* is *Myxococcus xanthus*.

In certain embodiments, the additional microbes are capable of fixing, solubilizing and/or mobilizing nitrogen, potassium, phosphorous (or phosphate) and/or other micronutrients in soil. In one embodiment, a nitrogen-fixing bacteria can be included, such as, for example, *Azotobacter vinelandii*. In another embodiment, a potassium-mobilizing bacteria can be included, such as, for example, *Frateuria aurantia*.

Other additional microbes can include, for example, *Pseudomonas chlororaphis, Wickerhamomyces anomalus, Starmerella bombicola, Saccharomyces boulardii, Pichia occidentalis, Pichia kudriavzevii*, and/or *Meyerozyma guilliermondii*.

The species and ratio of microorganisms and other ingredients in the composition can be customized using the computer-implemented methods described herein. In a specific embodiment, the MCS 10 identifies and recommends a specific formulation of microorganisms to be used in the composition.

The microbes and microbe-based soil treatment compositions of the subject invention have a number of beneficial properties that are useful for enhancing plant health, growth and/or yields. For example, the compositions can comprise products resulting from the growth of the microorganisms, such as biosurfactants, proteins and/or enzymes, either in purified or crude form.

Advantageously, in accordance with the subject invention, the soil treatment composition may comprise the medium in which each of the microorganism were grown. The composition may be, for example, at least, by weight, 1%, 5%, 10%, 25%, 50%, 75%, or 100% growth medium.

The fermentation medium can contain a live and/or an inactive culture, purified or crude form growth by-products, such as biosurfactants, enzymes, and/or other metabolites, and/or any residual nutrients. The amount of biomass in the composition, by weight, may be, for example, anywhere from about 0.01% to 100%, about 1% to 90%, about 5% to about 80%, or about 10% to about 75%.

The product of fermentation may be used directly, with or without extraction or purification. If desired, extraction and purification can be easily achieved using standard extraction and/or purification methods or techniques described in the literature.

The microorganisms in the soil treatment composition may be in an active or inactive form, or in the form of vegetative cells, reproductive spores, mycelia, hyphae, conidia or any other form of microbial propagule. The composition may also contain a combination of any of these microbial forms.

In one embodiment, different species of microorganism are grown separately and then mixed together to produce the soil treatment composition. In one embodiment, microorganisms can be co-cultivated, for example, *B. amyloliquefaciens* and *M. xanthus*.

In one embodiment, the composition is preferably formulated for application to soil, seeds, whole plants, or plant parts (including, but not limited to, roots, tubers, stems, flowers and leaves). In certain embodiments, the composition is formulated as, for example, liquid, dust, granules, microgranules, pellets, wettable powder, flowable powder, emulsions, microcapsules, oils, or aerosols.

To improve or stabilize the effects of the composition, it can be blended with suitable adjuvants and then used as such or after dilution, if necessary. In preferred embodiments, the composition is formulated as a liquid, a concentrated liquid, or as dry powder or granules that can be mixed with water and other components to form a liquid product.

In one embodiment, the composition can comprise glucose (e.g., in the form of molasses), glycerol and/or glycerin, as, or in addition to, an osmoticum substance, to promote osmotic pressure during storage and transport of the dry product.

The compositions can be used either alone or in combination with other compounds and/or methods for efficiently enhancing plant health, growth and/or yields, and/or for supplementing the growth of the first and second microbes. For example, in one embodiment, the composition can include and/or can be applied concurrently with nutrients and/or micronutrients for enhancing plant and/or microbe growth, such as magnesium, phosphate, nitrogen, potassium, selenium, calcium, sulfur, iron, copper, and zinc; and/or one or more prebiotics, such as kelp extract, fulvic acid, chitin, humate and/or humic acid. The exact materials and the quantities thereof can be determined by a grower or an agricultural scientist having the benefit of the subject disclosure.

The compositions can also be used in combination with other agricultural compounds and/or crop management systems. In one embodiment, the composition can optionally comprise, or be applied with, for example, natural and/or chemical pesticides, repellants, herbicides, fertilizers, water treatments, non-ionic surfactants and/or soil amendments.

If the composition is mixed with compatible chemical additives, the chemicals are preferably diluted with water prior to addition of the subject composition.

Further components can be added to the composition, for example, buffering agents, carriers, other microbe-based compositions produced at the same or different facility, viscosity modifiers, preservatives, nutrients for microbe growth, tracking agents, biocides, other microbes, surfactants, emulsifying agents, lubricants, solubility controlling agents, pH adjusting agents, preservatives, stabilizers and ultra-violet light resistant agents.

The pH of the microbe-based composition should be suitable for the microorganism of interest. In a preferred embodiment, the pH of the composition is about 3.5 to 7.0, about 4.0 to 6.5, or about 5.0.

Optionally, the composition can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C.

The microbe-based compositions may be used without further stabilization, preservation, and storage, however. Advantageously, direct usage of these microbe-based compositions preserves a high viability of the microorganisms, reduces the possibility of contamination from foreign agents and undesirable microorganisms, and maintains the activity of the by-products of microbial growth.

In other embodiments, the composition (microbes, growth medium, or microbes and medium) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 pint to 1,000 gallons or more. In certain embodiments the containers are 1 gallon, 2 gallons, 5 gallons, 25 gallons, or larger 6. Application of Soil and/or Crop Treatment Composition In preferred embodiments, a method for promoting agricultural productivity at a geographic site is provided, comprising applying a customized soil and/or crop treatment composition according to the subject invention to a plant or crop located at the site, and/or the plant or crop's surrounding environment.

In specific embodiments, the method comprises obtaining a soil and/or crop treatment composition according to the subject invention, wherein the composition comprises a customized formulation recommended by the MCS 10, and applying the composition to the plant, crop and/or its environment. In some embodiments, multiple plants, crops and/or their surrounding environments are treated according to the subject methods.

As used herein, a plant or crop's "surrounding environment" means the soil and/or other medium in which the plant or crop is growing, which can include the rhizosphere. In certain embodiments, the surrounding environment does not extend past, for example, a radius of at least 5 miles, 1 mile, 1,000 feet, 500 feet, 300 feet, 100 feet, 10 feet, 8 feet, or 6 feet from the plant or crop.

To improve or stabilize the effects of the treatment composition, it can be blended with suitable adjuvants and then used as such or after dilution if necessary. In preferred embodiments, the composition is formulated as a dry powder or as granules, which can be mixed with water and other components to form a liquid product.

In some embodiments, the methods further comprise applying materials with the composition to enhance microbe growth during application (e.g., nutrients and/or prebiotics to promote microbial growth). In one embodiment, nutrient sources can include, for example, sources of nitrogen, potassium, phosphorus, magnesium, proteins, vitamins and/or carbon. In one embodiments, prebiotics can include, for example, kelp extract, fulvic acid, chitin, humate and/or humic acid.

Additionally, in one embodiment, the method can be used to inoculate a rhizosphere with one or more beneficial microorganisms. For example, in some embodiments, when a biological soil treatment composition is applied comprising one or more microorganisms, the microorganisms can colonize the rhizosphere and provide multiple benefits to the plant whose roots are growing therein, including protection and nourishment.

In one embodiment, the method can enhance plant health, growth and/or yields by enhancing root health and growth. More specifically, in one embodiment, the methods can be used to improve the properties of the rhizosphere in which a plant's roots are growing, for example, the nutrient and/or moisture retention properties.

Advantageously, in one embodiment, the subject methods can be used to enhance health, growth and/or yields in plants having compromised immune health due to an infection from a pathogenic agent or from an environmental stressor, such as, for example, drought. Thus, in certain embodiments, the subject methods can also be used for improving the immune health, or immune response, of plants.

As used herein, "applying" a composition or product refers to contacting a composition or product with a target or site such that the composition or product can have an effect on that target or site. Applying can also include "treating" a target or site with a composition.

Application can further include contacting a composition directly with a plant, plant part, and/or the plant's surrounding environment (e.g., the soil or the rhizosphere). The composition can be applied as a seed treatment or to the soil surface, or to the surface of a plant or plant part (e.g., to the surface of the roots, tubers, stems, flowers, leaves, fruit, or flowers). It can be sprayed, poured, sprinkled, injected or spread as liquid, dry powder, dust, granules, microgranules, pellets, wettable powder, flowable powder, emulsions, microcapsules, oils, gels, pastes or aerosols.

In a specific embodiment, the composition is contacted with one or more roots of the plant. The composition can be applied directly to the roots, e.g., by spraying or dunking the roots, and/or indirectly, e.g., by administering the composition to the soil in which the plant grows (e.g., the rhizosphere). The composition can be applied to the seeds of the plant prior to or at the time of planting, or to any other part of the plant and/or its surrounding environment.

In certain embodiments, the compositions provided herein are applied to the soil surface without mechanical incorporation. The beneficial effect of the soil application can be activated by rainfall, sprinkler, flood, or drip irrigation, and subsequently delivered to, for example, the roots of plants.

Plants and/or their environments can be treated at any point during the process of cultivating the plant. For example, the composition can be applied to the soil prior to, concurrently with, or after the time when seeds are planted therein. It can also be applied at any point thereafter during the development and growth of the plant, including when the plant is flowering, fruiting, and during and/or after abscission of leaves.

In one embodiment, the method can be used in a large scale agricultural setting. The method can comprise administering the composition into a tank connected to an irrigation system used for supplying water, fertilizers or other liquid compositions to a crop, orchard or field. Thus, the plant and/or soil surrounding the plant can be treated with the composition via, for example, soil injection, soil drenching, or using a center pivot irrigation system, or with a spray over the seed furrow, or with sprinklers or drip irrigators. Advantageously, the method is suitable for treating hundreds of acres of crops, orchards or fields at one time.

In one embodiment, the method can be used in a smaller scale setting, such as in a home garden or greenhouse. In such cases, the method can comprise spraying a plant and/or its surrounding environment with the composition using a handheld lawn and garden sprayer. The composition can be mixed with water, and optionally, other lawn and garden treatments, such as fertilizers and pesticides. The composition can also be mixed in a standard handheld watering can and poured onto soil.

In certain embodiments, the plant receiving treatment is healthy. Advantageously, the subject invention can be useful in enhancing the immune response of a plant having a compromised immune system, for example, because the plant is affected by disease and/or disease symptoms. In one embodiment, the methods are used to enhance the health, growth and/or yields of citrus trees affected by citrus greening disease and/or citrus canker disease.

For example, the plant may be affected by a pathogenic strain of *Pseudomonas* (e.g., *P. savastanoi, P. syringae* pathovars); *Ralstonia solanacearum; Agrobacterium* (e.g., *A. tumefaciens*); *Xanthomonas* (e.g., *X. oryzae* pv. *Oryzae, X. campestris* pathovars, *X. axonopodis* pathovars); *Erwinia* (e.g., *E. amylovora*); *Xylella* (e.g., *X. fastidiosa*); *Dickeya* (e.g., *D. dadantii* and *D. solani*); *Pectobacterium* (e.g., *P. carotovorum* and *P. atrosepticum*); *Clavibacter* (e.g., *C. michiganensis* and *C. sepedonicus*); *Candidatus Liberibacter asiaticus; Pantoea; Burkholderia; Acidovorax; Streptomyces; Spiroplasma;* and/or *Phytoplasma*; as well as huanglongbing (HLB, citrus greening disease), citrus canker disease, citrus bacterial spot disease, citrus variegated chlorosis, brown rot, citrus root rot, citrus and black spot disease.

In one embodiment, the method controls pathogenic microorganisms themselves. In one embodiment, the method works by enhancing the immune health of plants to increase the ability to fight off infections.

In another embodiment, the method controls pests that might act as vectors or carriers for pathogenic bacteria, such as flies, aphids, ants, beetles, and whiteflies. Thus, the subject methods can prevent the spread of plant pathogenic bacteria by controlling, e.g., killing, these carrier pests.

The present invention can be used to improve the soil microbiome in or example, agricultural and/or horticultural settings, greenhouses, landscaping, and the like.

In one embodiment, the subject methods can be used for enhancing plant health, growth and/or yields; enhancing plant immunity and tolerance to abiotic and/or biotic stressors; enhancing carbon sequestration in soil; reducing emissions of greenhouse gases from agricultural activity; reducing the amount of chemical fertilizers, pesticides and/or other soil amendments required at a site; reducing water usage and runoff; reducing pest numbers and disease outbreaks; encouraging the presence and/or colonization of other beneficial above- and below-ground organisms, thus increasing biodiversity; and/or improving one or more physical and/or chemical qualities of soil, including dry, waterlogged, porous, depleted, compacted soils and/or combinations thereof.

The compositions can be used either alone or in combination with other compounds for efficient enhancement of plant health, growth and/or yields, as well as other compounds for efficient treatment and prevention of plant pathogenic pests. For example, the methods can be used concurrently with sources of nutrients and/or micronutrients for enhancing plant and/or microbe growth, such as magnesium, phosphate, nitrogen, potassium, selenium, calcium, sulfur, iron, copper, and zinc; and/or one or more prebiotics, such as kelp extract, fulvic acid, chitin, humate and/or humic acid. The exact materials and the quantities thereof can be determined by a grower or an agricultural scientist having the benefit of the subject disclosure.

The compositions can also be used in combination with other agricultural compounds and/or crop management systems. En one embodiment, the composition can optionally comprise, and/or be applied with, for example, natural and/or chemical pesticides, repellants, herbicides, fertilizers, water treatments, non-ionic surfactants and/or soil amendments.

In certain embodiments, the compositions and methods can be used to enhance the effectiveness of other compounds, for example, by enhancing the penetration of a pesticidal compound into a plant or pest, or enhancing the bioavailability of a nutrient to plant roots. The compositions can also be used to supplement other treatments, for example, antibiotic treatments. Advantageously, the subject invention helps reduce the amount of antibiotics that must be administered to a crop or plant in order to be effective at treating and/or preventing bacterial infection.

In one embodiment, the methods and compositions according to the subject invention lead to an increase in one or more of: root mass, trunk diameter, canopy density, brix value, chlorophyll content, flower count and/or leaf tissue nitrogen levels of a plant, by about 5%, 10%, 20%, 30%, 40%, 50%, 60% 70%, 80%, 90%, 100%, 150%, 200%, or more, compared to a plant growing in an untreated environment.

In one embodiment, the methods and compositions according to the subject invention lead to an increase in soil organic carbon content, by about 5%, 10%, 20%, 30%, 40%, 50%, 60% 70%, 80%, 90%, 100%, 150%, 200%, or more, compared to soil in an untreated environment.

In certain embodiments, the methods and compositions according to the subject invention lead to an increase in crop yield by about 5%, 10%, 20%, 30%, 40%, 50%, 60% 70%, 80%, 90%, 100%, 150%, 200%, or more, compared to untreated crops.

In one embodiment, the methods and compositions according to the subject invention lead to a reduction in the number of pests on a plant or in a plant's surrounding environment by about 55%, 10%, 20%, 30%, 40%, 50%, 60% 70%, 80%, 90%, 100%, 150%, 200%, or more, compared to a plant growing in an untreated environment.

In one embodiment, the methods and compositions according to the subject invention reduce damage to a plant caused by pests by about 5%, 10%, 20%, 30%, 40%, 50%, 60% 70%, 80%, 90%, 100%, 150%, 200%, or more, compared to plants growing in an untreated environment.

In preferred embodiments, the subject invention is used for promoting agricultural productivity of crop plants. As used herein, "crop plants" refer to any species of plant or alga edible by humans or used as a feed for animals or fish or marine animals, or consumed by humans, or used by humans (e.g., textile or cosmetics production), or viewed by humans (e.g., flowers or shrubs in landscaping or gardens) or any plant or alga, or a part thereof, used in industry or commerce or education.

Examples of crop plants for which the invention is useful include, but are not limited to, cereals and grasses (e.g., wheat, barley, rye, oats, rice, maize, sorghum, corn, and sod); beets (e.g., sugar and fodder beets); fruit crops (e.g., plants bearing pomaceous fruits, stone fruits, soft fruits, berries, tomatoes, grapes, mango, strawberries, peaches, apples, pears, plums, almonds, bananas, citrus and cherries); leguminous crops (e.g., peanuts, beans, lentils, peas and soya); oil crops (e.g., oilseed, rapeseed, mustard, poppies, olive, soybean, palm, sunflower, coconut, castor, cocoa and ground nuts); cucurbits (e.g., pumpkins, cucumbers, squash and melons); fiber plants (e.g., cotton, flax, hemp and jute); leafy vegetables (e.g., spinach, lettuce, kale and cabbage); root and tuber vegetables (e.g., carrots, parsnips, onions, potatoes, sweet potatoes and yams); Lauraceae (e.g., avocado, Cinnamonium and camphor); and tobacco, nut-bearing plants, herbs, spices, medicinal plants, cacao, cassava, coffee, asparagus, chilies, peppers, eggplants, sugarcane, tea, hops, the plantain family, latex plants, rubber plants, ornamentals, flowers for cutting, and any relatives thereof.

Growth of Microbes According to the Subject Invention

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. These cultivation processes include, but are not limited to, submerged cultivation/fermentation, solid state fermentation (SSF), and modifications, hybrids and/or combinations thereof.

As used herein "fermentation" refers to cultivation or growth of cells under controlled conditions. The growth could be aerobic or anaerobic. In preferred embodiments, the microorganisms are grown using SSF and/or modified versions thereof.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, humidity, microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of organisms in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. In the case of submerged fermentation, the oxygenated air may be ambient air supplemented daily through mechanisms including impellers for mechanical agitation of liquid, and air spargers for supplying bubbles of gas to liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, canola oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, sodium chloride, calcium carbonate, and/or sodium carbonate. These inorganic salts may be used independently or in a combination of two or more.

In some embodiments, the method for cultivation may further comprise adding additional acids and/or antimicrobials in the medium before, and/or during the cultivation process. Antimicrobial agents or antibiotics are used for protecting the culture against contamination.

Additionally, antifoaming agents may also be added to prevent the formation and/or accumulation of foam during submerged cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the medium may be necessary.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesirable bacterial growth.

In one embodiment, the subject invention further provides a method for producing microbial metabolites such as, for example, biosurfactants, enzymes, proteins, ethanol, lactic acid, beta-glucan, peptides, metabolic intermediates, polyunsaturated fatty acid, and lipids, by cultivating a microbe strain of the subject invention under conditions appropriate for growth and metabolite production; and, optionally, purifying the metabolite. The metabolite content produced by the method can be, for example, at least 20%, 30%, 40%, 50%, 60%, 70%, 80%, or 90%.

The microbial growth by-product produced by microorganisms of interest may be retained in the microorganisms or secreted into the growth medium. The medium may contain compounds that stabilize the activity of microbial growth by-product.

The biomass content of the fermentation medium may be, for example, from 5 g/l to 180 g/l or more, or from 10 g/l to 150 g/l.

The cell concentration may be, for example, at least $1\times10^6$ to $1\times10^{12}$, $1\times10^7$ to $1\times10^{11}$, $1\times10^8$ to $1\times10^{10}$, or $1\times10^9$ CFU/ml.

The method and equipment for cultivation of microorganisms and production of the microbial by-products can be performed in a batch, a quasi-continuous process, or a continuous process.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells, spores, conidia, hyphae and/or mycelia remains in the vessel as an inoculant for a new cultivation batch. The composition that is removed can be a cell-free medium or contain cells, spores, or other reproductive propagules, and/or a combination of thereof. In this manner, a quasi-continuous system is created.

Advantageously, the method does not require complicated equipment or high energy consumption. The microorganisms of interest can be cultivated at small or large scale on site and utilized, even being still-mixed with their media.

Advantageously, the microbe-based products can be produced in remote locations. The microbe growth facilities may operate off the grid by utilizing, for example, solar, wind and/or hydroelectric power.

Preparation of Microbe-Based Products

One microbe-based product of the subject invention is simply the fermentation medium containing the microorganisms and/or the microbial metabolites produced by the microorganisms and/or any residual nutrients. The product of fermentation may be used directly without extraction or purification. If desired, extraction and purification can be easily achieved using standard extraction and/or purification methods or techniques described in the literature.

The microorganisms in the microbe-based products may be in an active or inactive form, or in the form of vegetative cells, reproductive spores, conidia, mycelia, hyphae, or any other form of microbial propagule. The microbe-based products may also contain a combination of any of these forms of a microorganism.

In one embodiment, different strains of microbe are grown separately and then mixed together to produce the microbe-based product. The microbes can, optionally, be blended with the medium in which they are grown and dried prior to mixing.

In one embodiment, the different strains are not mixed together, but are applied to a plant and/or its environment as separate microbe-based products.

The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

Upon harvesting the microbe-based composition from the growth vessels, further components can be added as the harvested product is placed into containers or otherwise transported for use. The additives can be, for example, buffers, carriers, other microbe-based compositions produced at the same or different facility, viscosity modifiers, preservatives, nutrients for microbe growth, surfactants, emulsifying agents, lubricants, solubility controlling agents, tracking agents, solvents, biocides, antibiotics, pH adjusting agents, chelators, stabilizers, ultra-violet light resistant agents, other microbes and other suitable additives that are customarily used for such preparations.

In one embodiment, buffering agents including organic and amino acids or their salts, can be added. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

The pH of the microbe-based composition should be suitable for the microorganism(s) of interest. In a preferred embodiment, the pH of the composition is about 3.5 to 7.0, about 4.0 to 6.5, or about 5.0.

In one embodiment, additional components such as an aqueous preparation of a salt, such as sodium bicarbonate or carbonate, sodium sulfate, sodium phosphate, sodium biphosphate, can be included in the formulation.

In certain embodiments, an adherent substance can be added to the composition to prolong the adherence of the product to plant parts. Polymers, such as charged polymers, or polysaccharide-based substances can be used, for example, xanthan gum, guar gum, levan, xylinan, gellan gum, curdlan, pullulan, dextran and others.

In preferred embodiments, commercial grade xanthan gum is used as the adherent. The concentration of the gum should be selected based on the content of the gum in the commercial product. If the xanthan gum is highly pure, then 0.001% (w/v—xanthan gum/solution) is sufficient.

In one embodiment, glucose, glycerol and/or glycerin can be added to the microbe-based product to serve as, for example, an osmoticum during storage and transport. In one embodiment, molasses can be included.

In one embodiment, prebiotics can be added to and/or applied concurrently with the microbe-based product to enhance microbial growth. Suitable prebiotics, include, for example, kelp extract, fulvic acid, chitin, humate and/or humic acid. In a specific embodiment, the amount of prebiotics applied is about 0.1 L/acre to about 0.5 L/acre, or about 0.2 L/acre to about 0.4 L/acre.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a citrus grove). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This allows for a scaled-down bioreactor (e.g., smaller fermentation vessel, smaller supplies of starter material, nutrients and pH control agents), which makes the system efficient and can eliminate the need to stabilize cells or separate them from their culture medium. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

Advantageously, the compositions can be tailored for use at a specified location. In one embodiment, the microbe growth facility is located on, or near, a site where the microbe-based products will be used (e.g., a citrus grove).

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products to improve agricultural production.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention.

Example 1—Computer Generated Recommendation for Agronomic Programs Using Soil Samples Aspects of FIG. 1 and FIG. 3 are referenced in this Example. The Algorithm Development (AD) module 20 receives a Training Data Set 101 comprising DNA sequencing data derived from soil samples (not shown) taken from a plurality of geographic sites. The Training Data Set 101 provides a relative frequency of taxonomic-indicating and/or function-indicating gene markers within the tested soil samples, thereby providing a relative frequency of soil microbial species and/or gene functions in each sample.

The Unsupervised Machine Learning Classifier (UMLC) 102 analyzes the Training Data Set 101 and classifies each soil sample by microbiome "type" 102*a* based upon similarities between the samples. The similarities can include relative frequencies of taxonomical units, functional gene sequences, or other information derived from the DNA sequencing data of the Training Data Set 101.

Other agronomic training data is then received by the AD module 20, comprising environmental training data 103 and microbe soil test training data 104. The environmental training data 103 can include, for example, soil type (e.g., sandy, loam, clay, silt, etc.), soil composition/characteristics (e.g., moisture, pH, nutrient content, mineral content), and/or crop data (e.g., past and/or current crops grown at a geographic site).

The microbial test training data 104 is generated by lab tests or in-field tests (see FIG. 2 and Example 2) conducted by the user or by a third party. These tests provide quantitative reports of indicator gene-markers or species of microbes in the soil samples, i.e., the microbial test training data 104.

The Supervised Machine Learning Classifier (SMLC) 105, which can be housed in a Centralized Computer and Database system 30, is developed using the classification (soil microbiome type) data 102a generated by the UMLC 102, the environmental training data 103, and the microbial test training data 104. The environmental training data 103 and the microbial test training data 104 are used to "train" the SMLC 105 to generate microbiome type predictions 105a for a specific geographic site 60 based on site-specific prediction input data 103a, 104a.

The Recommendation Engine 106 correlates the predicted microbiome type(s) 105a with an optimal agronomic program 107 for a specific geographic site 60 (see FIG. 3 and Example 3). A Supervised Machine Learning Predictor ("SMLP") 302, which identifies the statistically impactful relationships between predicted soil type classification 105a, site-specific environmental data 103a, and an agronomic metric of interest (e.g., yield, soil carbon sequestration, brix value, fruit size, NDVI, etc.) 301. The SMLP 302 then identifies candidate agricultural products 304a and/or activities that can have a statistically relevant impact on the agronomic metric of interest 301 to promote agricultural productivity.

Following the implementation of one or more recommended agronomic programs 107 at a specific geographic site 60, the program 107 and its results 108 are recorded and submitted back into the Recommendation Engine 106, to validate the impact of the agronomic program 107 on the agronomic metric of interest 301 and further improve the recommendation capabilities of the system 10.

Example 2—Constructing Microbial Test Data

Aspects of FIG. 2, which depicts a block/flow diagram of methods for obtaining microbial test data 41, are referenced in this Example. The microbial test data 104, 104a comprises quantitative measurements of microorganisms, including population numbers and/or proportions, as well as gene function frequencies, in a sample.

Field-based assays are one method for obtaining quantitative data regarding microbial species, gene markers, and/or gene functions present in a sample. A paper-based field assay 42 involves a chemical label (e.g., a dye, fluorescing agent, up-converting phosphor particles (UCPs)) 205 that produces a signal (e.g., color change, fluorescence or luminescence) 205a based on the concentration of a target analyte (e.g., DNA, protein, antibody or microbe) in a sample (e.g., soil). The label 205 and the sample are applied to a paper component so that they can contact one another to produce the signal 205a.

Two forms of paper-based field assays include Flow-Through 206 and Lateral Flow 207 assays. Both comprise a paper reactive membrane that produces the signal 205a when contacted with the sample, and an absorbent membrane that absorbs excess liquid sample.

A diagnostic reader 43 can be used to process the results of the paper-based field assay 42. The method for reading the result (optical 203 or image-based 204) will be dependent upon the spectrum in which the label 205 emits a signal (e.g., visible, UV, or IR radiation) 205a.

A data processing algorithm 44 then takes raw data 203a, 204a generated from the diagnostic reader and normalizes it relative to its background noise and known quantitative control signals. This layer can exist within the diagnostic reader 43 or in a separate software layer (not shown).

Along with paper-based assay systems 42, lab-based assays 45 can also provide similar microbe soil test data. These assays, e.g., DNA-sequencing 208, immunoassays 209, and culture-based assays 210, are performed using traditional lab-based protocols and equipment.

Example 3—Development of Recommendation Engine for New Product Discovery

Aspects of FIG. 1 and FIG. 3 are referred to in this Example. The Recommendation Engine 106 is used to generate recommendations for agronomic programs 107. The agronomic program 107 can include a customized formulation for a new product, or soil and/or crop treatment composition, for applying to a geographic site 60.

A Supervised Machine Learning Predictor ("SMLP") 302 receives, as input data, predicted microbiome type classification 105a, site-specific environmental data 103a, and an agronomic metric of interest (e.g., yield, soil carbon sequestration, brix value, fruit size, NDVI, etc.) 301 for a specific geographic site 60; and identifies the statistically impactful relationships between the predicted classification 105a and/or site-specific environmental data 103a, and the agronomic metric 301.

The SMLP 302 produces as output, the identities of key predicted microbiome classifications 105a and in turn, identifies candidate microorganisms 303 based on gene functions and/or taxonomic units that have statistically relevant impacts on the agronomic metric of interest 301.

The candidate microorganisms are then screened 304 for their ability to be fermented and produced at the scale needed for application at the geographic site, as well as their ability to be formulated and transported for application by the user as an efficacious product. The microbes can also be referenced against and/or included in a known library of fermentable and productizable strains. The screening results are also fed back into the Recommendation Engine 106 to be useful for future microbial candidate selection.

A formulation 304a for a composition is then generated. After production of the composition, it can be applied to the geographic site for field trials and experimentation 305 to, for example, confirm the impact of the composition on the agronomic metric of interest 301. The results of the trials can be recorded and submitted back into the Recommendation Engine 106, to further improve the recommendation capabilities of the system 10.

Example 4—Scenario: New Product Discovery for Citrus Using Soil Samples

Aspects of FIG. 1 and FIG. 3 are referred to in this Example. Various citrus plots 60 and their associated site-specific environmental data 103a and site-specific microbial test data 104a are processed through the SMLC 105. Each plot 60 is classified, meaning a prediction of the soil microbiome "type" 105a is assigned to each plot. Based upon the predicted classification 105a, generalized distributions of bacterial and fungal species are identified for the soil of each plot 60. It is revealed that half of the plots 60 are lacking in a particular consortium of microbial species.

Through controlled experiments and trials 305, it is discovered that one or multiple species exist that help suppress the negative impacts associated with the citrus greening pathogen, *Candidatus Liberibacter* spp. This new discovery is incorporated into the Recommendation Engine 106. The effective species are also screened 304 for scaled-up fermentation capabilities.

If classification of future citrus soils 60 reveals a lack of the newly discovered beneficial species, the resulting recommendation for soil treatment compositions will comprise formulations 304a inclusive of those species and any materials (e.g., nutrients and/or prebiotics) that support them.

Example 5—Scenario: Corn and Flood Event Using Soil Samples

Aspects of FIG. 1 and FIG. 3 are referred to in this Example. Midwest corn fields 60 and their associated site-specific environmental data 103a and site-specific microbial test data 104a are processed through the SMLC 105. Each field 60 is classified, meaning a prediction of the soil microbiome "type" 105a is assigned to each field.

A recent flood event has left the fields 60 saturated with water for multiple weeks. Altering the site-specific environmental data 103a to reflect the high levels of rain and soil moisture and re-processing the SMLC 105 results in new predicted classifications 105a that are non-optimal for corn production.

The Recommendation Engine 106 recommends new product formulations 304a based on the new predicted classifications 105a to help shift the soil microbiome to optimal growing conditions, given the anaerobic conditions that evolved and the likely increase in fungal population in the soil. The Recommendation Engine 106 also recommends application of a fungicide prior to application of the new product formulations 304a in order to maximize the likelihood of establishing a colony of the beneficial microorganisms in the soil.

Example 6—Scenario: Soil Carbon Aggregation

Aspects of FIG. 1 and FIG. 3 are referred to in this Example. To maximize the aggregation of organic carbon in agricultural soils, the soils 60 and their associated site-specific environmental data 103a and site-specific microbial test data 104a are processed through the SMLC 105. Certain influential site-specific environmental data include, for example, cover crop, crop type, fallow, tilling practices, and irrigation practices. The Recommendation Engine 106 recommends new product formulations 304a that will ensure the highest conversion of carbon dioxide to soil organic carbon.

Separate formulations 304a can also be recommended to minimize nitrous oxide and methane emissions. These formulations 304a can be tuned given the economic incentives that may be in place to encourage carbon sequestration or emissions reductions. These formulations 304a could also be tuned to account for the potential tradeoff between optimizing for carbon related income and traditional agriculture related income.

Example 7—Scenario: Weather and Potato Fields

Aspects of FIG. 1 and FIG. 3 are referred to in this Example. Idaho potato fields 60 and their associated site-specific environmental data 103a and site-specific microbial test data 104a are processed through the SMLC 105. Each field 60 is classified, meaning a prediction of the soil microbiome "type" 105a is assigned to each field.

Shortly after planting, a late freeze occurs in some areas of the potato fields 60. Given this change, the system 10 produces a new predicted classification 105a that is non-optimal for potato production.

The Recommendation Engine 106 recommends new product formulations 304 based on the new predicted classifications 105a and the changing weather input data 103a. For areas with the late freeze, the formulation 304a includes soil microorganisms capable of metabolic activity in lower temperatures to support root growth. The Recommendation Engine 106 also recommends the application of those product formulations 304a to be applied in early morning, when temperatures are low, to maximize the opportunity for the microorganisms to outcompete native populations that do not thrive at those temperatures.

REFERENCES

Mewes et al. "Modeling and Prediction of Below-Ground Performance of Agricultural Biological Products in Precision Agriculture." U.S. Patent Application Publication No. 2019/0050741 A1.
Thompson, et al. (2017) "A communal catalogue reveals Earth's Multiscale microbial diversity." *Nature*. 551:457-63.
Xiang et al. "Estimating Soil Properties Within a Field Using Hyperspectral Remote Sensing." U.S. Patent Application Publication No. 2017/0090068 A1.

We claim:

1. A method, using a computer system, for recommending an agronomic program for a specific geographic site for the purpose of promoting soil carbon sequestration at the specific geographic site, the method comprising:
   obtaining a Training Data Set comprising DNA sequencing data derived from each of a plurality of soil, plant, water and/or air samples taken from a plurality of geographic sites, wherein said DNA sequencing data provides relative frequencies of taxonomic-indicating and/or function-indicating microbial gene markers in the each of the plurality of soil, plant, water and/or air samples taken from the plurality of geographic sites;
   inputting the Training Data Set into an Algorithm Development (AD) module, wherein the AD module comprises an Unsupervised Machine Learning Classifier (UMLC);
   developing, using the UMLC, a classification model that assigns microbiome classifications to the each of the plurality of soil, plant, water and/or air samples based upon similarities between relative frequencies of the taxonomic-indicating microbial gene markers and/or the function-indicating microbial gene markers in the each of the plurality of soil, plant, water and/or air samples;
   inputting environmental training data and microbial test training data from the each of the plurality of soil, plant, water and/or air samples into the AD module;
   developing, using a Supervised Machine Learning Classifier (SMLC), a predictive classifier model based on relationships between the assigned microbiome classifications, the environmental training data, and the microbial test training data from the each of the plurality of soil, plant, water and/or air samples;
   inputting, using the SMLC, site-specific prediction data collected from the specific geographic site into the predictive classifier model to predict microbiome classifications for soil, plant, water and/or air located at the specific geographic site, wherein the site-specific prediction data is site-specific environmental prediction data and site-specific microbial test prediction data from the specific geographic site;

correlating, using a Recommendation Engine, the predicted microbiome classifications for the specific geographic site with a recommended agronomic program, wherein the Recommendation Engine uses a Supervised Machine Learning Predictor to identify statistically impactful relationships between the predicted microbiome classifications, the site-specific prediction data, and soil carbon sequestration to identify agricultural activities and/or agricultural products that have a statistically relevant impact on promoting soil carbon sequestration at the specific geographic site, and wherein the recommended agronomic program comprises a list and/or schedule of the agricultural activities identified and/or one or more customized microbial soil treatment compositions to apply at the specific geographic site to promote soil carbon sequestration;

implementing the recommended agronomic program at the specific geographic site; and conducting field trials and experimentation at the specific geographic site to determine an impact of the recommended agronomic program on the promoting soil carbon sequestration.

2. The method of claim 1, wherein the DNA sequencing data is derived from the each of the plurality of soil samples from the plurality of geographic sites.

3. The method of claim 1, wherein the environmental training data and/or site-specific environmental prediction data comprise one or more of location, weather and/or climate data, soil type, soil composition, soil characteristics, crop data, agricultural supplementation and/or irrigation practices, crop imagery and/or diagnostic data, historical non-agricultural land activity, pests, invasive and non-invasive flora and fauna, and natural and man-made landmarks.

4. The method of claim 3, wherein the environmental training data and/or site-specific environmental prediction data are soil type, soil characteristics, irrigation practices, tilling practices, and crop data, wherein the crop data is selected from crop type, cover crop usage, and fallow history.

5. The method of claim 1, wherein the microbial test training data provides quantitative reports of taxonomic-indicating and/or function-indicating microbial gene markers, and/or quantitative microbe counts, in the each of the soil, plant, water and/or air samples obtained from the plurality of geographic sites, and wherein the site-specific microbial test prediction data provides quantitative reports of taxonomic-indicating and/or function-indicating microbial gene markers, and/or quantitative microbe counts, in soil, plant, water and/or air samples obtained from the specific geographic site for which the agronomic program is being recommended.

6. The method of claim 5, wherein the microbial test training data is obtained using field assays and/or lab-based assays of the each of the plurality of soil, plant, water and/or air samples obtained from the plurality of geographic sites, and wherein the site-specific microbial test prediction data is obtained using field assays and/or lab-based assays of soil, plant, water and/or air samples obtained from the specific geographic site for which the agronomic program is being recommended.

7. The method of claim 1, wherein the site-specific environmental data is altered when a change in the environment occurs at the specific geographic site, wherein the SMLC is re-processed with the altered site-specific environmental data to produce new predicted microbiome classifications, and wherein the Recommendation Engine recommends a new agronomic program based on the new predicted microbiome classifications.

8. The method of claim 1, wherein the one or more customized microbial soil treatment compositions comprises one or more of the following microorganisms: *Trichoderma harzianum, Bacillus amyloliquefaciens, Bacillus subtilis, Myxococcus xanthus, Wickerhamomyces anomalus, Azotobacter vinelandii, Frateuria aurantia, Pseudomonas chlororaphis, Starmerella bombicola, Saccharomyces boulardii, Pichia occidentalis, Pichia kudriavzevii,* and/or *Meyerozyma guilliermondii.*

* * * * *